United States Patent [19]
Cowings

[11] Patent Number: 5,694,939
[45] Date of Patent: Dec. 9, 1997

[54] AUTOGENIC-FEEDBACK TRAINING EXERCISE (AFTE) METHOD AND SYSTEM

[75] Inventor: Patricia S. Cowings, Saratoga, Calif.

[73] Assignee: The United States of America as represented by the Administrator of the National Aeronautics and Space Administration, Washington, D.C.

[21] Appl. No.: 543,093

[22] Filed: Oct. 3, 1995

[51] Int. Cl.$^6$ ............................................. A61B 5/02
[52] U.S. Cl. ........................ 128/671; 125/905; 600/27
[58] Field of Search .................................. 128/731, 732, 128/905, 630, 671; 600/26, 27, 28

[56] References Cited

U.S. PATENT DOCUMENTS

| | | | |
|---|---|---|---|
| 3,942,516 | 3/1976 | Glynn et al. | 128/732 |
| 4,819,656 | 4/1989 | Spector | 128/905 |
| 4,919,143 | 4/1990 | Ayers | 128/905 |
| 5,007,430 | 4/1991 | Dardik | 128/905 |
| 5,267,942 | 12/1993 | Saperston | 128/905 |
| 5,291,894 | 3/1994 | Nagy | 128/732 |
| 5,304,112 | 4/1994 | Mrklas et al. | 600/27 |
| 5,406,957 | 4/1995 | Tansey | 128/732 |

OTHER PUBLICATIONS

The Relationship of Motion Sickness Susceptibility to Learned Autonomic Control for Symptom Suppression, Patricia S. Cowings, et al. Aviation, Space and Environmental Medicine, pp. 570–575, Jun. 1982.

Transference of Learned Autonomic Control for Symptom Suppression Across Opposite Directions of Coriolis Acceleration, Toscano et al., NASA Ames Research Center report.

Motion and Space Sickness, Editor George H. Crampton, Chapter 17, by Patricia S. Cowings, pp. 353–372, titled Autogenic–Feedback Training: A Treatment for Motion and Space Sickness.

General Autonomic Components of Motion Sickness, Patricia S. Cowings et al., Psychophysiology, The Society for Psychophysiological Research, Inc, vol. 23, No. 5, pp. 542–551.

(List continued on next page.)

*Primary Examiner*—Lee S. Cohen
*Assistant Examiner*—Eric F. Winakur
*Attorney, Agent, or Firm*—Kenneth L. Warsh; Harry Lupuloff; John G. Mannix

[57] ABSTRACT

The autogenic-feedback training exercise (AFTE) method of the present invention is a combined application of physiologic and perceptual training techniques, such as autogenic therapy and biofeedback. This combined therapy approach produces a methodology that is appreciably more effective than either of the individual techniques used separately. The AFTE method enables sufficient magnitude of control necessary to significantly reduce the behavioral and physiologic reactions to severe environmental stressors. It produces learned effects that are persistent over time and are resistant to extinction and it can be administered in a short period of time. The AFTE method may be used efficiently in several applications, among which are the following: to improve pilot and crew performance during emergency flying conditions; to train people to prevent the occurrence of nausea and vomiting associated with motion and sea sickness, or morning sickness in early pregnancy; as a training method for preventing or counteracting air-sickness symptoms in high-performance military aircraft; for use as a method for cardiovascular training, as well as for multiple other autonomic responses, which may contribute to the alleviaton of space motion sickness (SMS) in astronauts and cosmonauts; training people suffering from migraine or tension headaches to control peripheral blood flow and reduce forehead and/or trapezius muscle tension; training elderly people suffering from fecal incontinence to control their sphincter muscles; training cancer patients to reduce the nauseagenic effects of chemotherapy; and training patients with chronic intestinal pseudo-obstruction (CIP).

31 Claims, 21 Drawing Sheets

OTHER PUBLICATIONS

Observed Differences in Learning Ability of Heart Rate Self-Regulation as a Function of Hypnotic Susceptibility, P.S. Cowings, NASA Ames Research Center Report, pp. 221–226.

Autogenic Feedback Training Improves Pilot Performance During Emergency Flying Conditions, Michael Kellar et al., Flight Safety Digest, pp. 1–11, Jul. 1993.

Autogenic–Feedback Training: A Potential Treatment for Orthostatic Intolerance In Aerospace Crews, Journal of Clinical Pharmacology, vol. 34, pp. 559–608, 1994.

Reliability of Psychophysiological Responses Across Multiple Motion Sickness Stimulation Tests, Cynthia Stout et al., Journal of Vestibular Research, vol. 5, No. 1, pp. 25–33, 1995.

AUTOGENIC-FEEDBACK TRAINING EXERCISE (AFTE) METHOD AND SYSTEM

ORIGIN OF INVENTION

The invention described herein was made by an employee of the United States Government and may be manufactured and used by or for the Government for governmental purposes without payment of any royalties thereon or therefor.

BACKGROUND Of THE INVENTION

1. Technical Field of the Invention

The present invention generally relates to a multi-parameter physiological conditioning method and apparatus, and particularly to an autogenic-feedback training exercise method for training people to gain better control of specific physiological responses. More particularly, the present invention combines two self-regulatory techniques, biofeedback and autogenic exercises, and permits subjects to voluntarily control several of their own autonomic responses simultaneously.

2. Description of the Prior Art

Space motion sickness, also referred to as Space Adaptation Syndrome (SAS), is a disorder which produces symptoms similar to those of motion sickness on Earth. This syndrome has affected a significant number of astronauts and cosmonauts exposed to microgravity in space, but it differs from what is commonly known as motion sickness in a number of critical ways. There is currently no ground-based method for predicting susceptibility to motion sickness in space. Biomedical data from past space missions indicate that some individuals who have had wide exposure to motion devices and acceleratory forces on Earth or in an aircraft, and who have never previously shown any tendency to develop motion sickness symptoms, were severely debilitated in the microgravity environment. Conversely, some individuals who had a history of susceptibility to motion sickness were unaffected by symptoms in space. Symptom episodes vary from mild discomfort to repeated vomiting, and sometimes occur suddenly, with little or no vomiting. The earliest recorded episode began within only seven minutes of orbit insertion, and malaise has been reported to last anywhere from one to five days.

Two types of countermeasures have been tested extensively, anti-motion sickness drugs and preflight protective adaptation (i.e., repeated exposures to motion-sickness-inducing stimuli). Anti-motion sickness drugs have had limited success in preventing or counteracting SAS, and frequently have caused debilitating side effects. Some of the disadvantages of protective adaptation training are: (1) it is expensive and presents practical scheduling (of crewmen) difficulties because of requirements for other training during the preflight period, (2) individuals who are highly susceptible to motion sickness tend to adapt slowly (if at all), and (3) there is relatively little transfer of "protection" across different types of stimuli. Finding a solution to this biomedical problem has become a very high priority goal of the manned space-flight program because of its potential impact on crew safety, comfort, and operational efficiency during shuttle missions.

One method of treatment that has been developed by the present applicants is referred to as Autogenic-Feedback Training (AFT), a combination of biofeedback and autogenic therapy which involves training physiological self-regulation as an alternative to pharmacological management. The rationale for using AFT is based on the observation that there are profound autonomic nervous system (ANS) changes associated with the motion sickness disorder. A principal thesis of the application of AFT is that learned control of autonomic response levels results in significant increases in motion sickness tolerance after training.

The importance of ANS responses in understanding and treating motion sickness has been a matter of some controversy. Some authors, in their review of motion sickness research, discussed many possible ANS changes during motion sickness, and noted that there was little consistency in either procedures used or results of the available research, and pointedly argued against the importance of ANS in motion sickness, stating that to the extent that motion sickness is nausea and vomiting, it is not an autonomic phenomenon and it cannot be considered a development of the autonomic effects of vestibular stimulation.

Other authors investigated the relationship between motion sickness symptomatology and blood pressure, heart rate, and body temperature, and concluded that such physiological measures appear to have little value in assessing or diagnosing the severity of motion sickness. This lack of correlation means that the use of physiological training procedures to control these physiological measures is likely to be of little value in preventing symptoms of motion sickness.

Yet some authors suggest that there is a strong sympathetic nervous system (SNS) component involved in the development of motion sickness, and others believe that changes in parasympathetic nervous system (PNS) activity are more descriptive of the development of the motion sickness syndrome.

Biofeedback or autogenic therapy have been used to prevent or reduce the symptoms of motion sickness, with a certain degree of success. However, it has been demonstrated that significantly better and faster results can be achieved using the combined biofeedback-autogenic training (AFT) method. When operant conditioning is used to train human subjects to voluntarily control autonomic responses, the process is often called biofeedback. This procedure consists of presenting a subject with augmented sensory information about the ongoing activity levels of some physiological response in his/her own body, such as by displaying the heart rate on a digital panel meter. The subject is rewarded whenever such levels change in a direction selected by the trainer, i.e., an increase in the heart rate above baseline. Most trainers provide the subject with instructions or suggestions as to how the desired response may be achieved. For example, remembering an exciting situation should result in accelerated pulse rate. Although the specific type of instruction provided may vary, this process usually results in an improved ability of the subject to modify his/her own response levels for longer periods of time. Like most learning situations, only repetition and practice are required before voluntary control is achieved. Eventually, the external feedback signals can be removed and sufficient control is maintained.

Autogenic therapy is an alternative technique wherein cognitive imagery is used to gain control over previously involuntary responses. The subject is taught a series of self-suggestion exercises which are designed to induce specific bodily sensations (such as warmth in the hands or feet) associated with a measurable physiological change such as peripheral vasodilation.

However, it would be desirable to provide an AFT exercise training methodology that uses the combination of biofeedback and autogenic therapy, and which is appreciably more effective than either of the biofeedback or the autogenic therapy used alone.

SUMMARY OF THE INVENTION

The present invention provides a unique (AFTE) autogenic-feedback multi-parameter physiological conditioning method and system for training people to gain better control of specific physiological responses, in a relatively very short period of time.

The AFTE method combines two self-regulatory techniques, biofeedback and Autogenic therapy, and permits subjects to voluntarily control several of their own autonomic responses simultaneously.

Yet another advantage presented by the present invention is that it enables subjects to normalize their individual ANS profiles. For instance, subjects are trained to simultaneously modify and control the hierarchy, magnitude and phase relationship of several physiological responses, aiming at keeping the levels of their physiological responses at, or close to baseline, under stress, in order to alleviate or prevent developing symptoms.

A further advantage of the present invention is the ability to extrapolate the use of the AFTE methodology and system for controlling various physiological responses in order to prevent or counteract various physiological symptoms.

Yet another feature of the present invention is that it enables the transfer of autonomic control for symptoms prevention or counteraction learned under training conditions to other more practical conditions, such as the control of airsickness in military pilots.

Briefly, the foregoing and other features of the present invention are achieved by providing a unique autogenic-feedback method and associated system. The AFTE method uses the combination of biofeedback and autogenic therapy, and is appreciably more effective than either of the biofeedback or the autogenic therapy used alone. Consequently, the time normally spent by the subject using a trial and error strategy is shortened, and the initial probability of making a correct response is substantially increased. Autogenic exercises provide the subject with a specific set of instructions, and method of concentration which is likely to produce the desired response. Biofeedback complements the autogenic exercises by providing immediate sensory information to the subject about the magnitude and direction of a response, and because operant conditioning procedures allow for more precise control of a response, the ultimate effectiveness is significantly increased.

It has been experimentally determined that physiological self-regulation can be further enhanced when both visual and/or auditory tone feedback are presented for each autonomic variable. During a typical training session a subject practicing control of a pattern of physiological responses may be monitoring one or more different feedback displays. This procedure requires additional training in attending to a complex set of visual and auditory feedback signals. Verbal instructions by a trainer may be required to direct the attention of the subject to specific feedback signals and to advise him/her of alternate strategies when an inappropriate response has occurred.

Therefore, the present invention proposes a new behavioral training procedure which reliably increases tolerance to, minimizes the symptoms resulting from, or solving the problems of motion sickness, SAS, sea sickness. This training procedure (AFTE) may also be used to attain better control of specific physiological responses. The effectiveness of AFTE is significantly better than that which can be obtained from protective adaptation training (i.e., repeated exposures to motion sickness tests). Highly susceptible subjects are just as likely to derive benefit from this training procedure as moderate or low motion sickness susceptible subjects. Data have been obtained that show no apparent effect from AFTE on measures of vestibular perception and no side effects, as could be the case with the most commonly used anti-motion sickness medications. The training effect has been demonstrated to transfer successfully to different types of nauseogenic conditions, including cross-coupled angular acceleration, linear motion, and visual stimulation. Additionally, preliminary data from space indicates that AFTE may be an effective countermeasure for space motion sickness SMS.

The present AFTE method can be effective for many people, despite their initial susceptibility to provocative motion sickness stimuli. It can reliably transfer to other stimulus conditions, and requires a short learning time.

The AFTE method may be used successfully and efficiently in several applications, among which are the following:

1. To improve pilot and crew performance during emergency flying conditions.
2. To train people to prevent the occurrence of nausea and vomiting as associated with motion and sea sickness, or morning sickness in early pregnancy.
3. As a training method for preventing or counteracting air-sickness symptoms in high-performance military aircraft.
4. For use as a method for cardiovascular training, as well as for multiple other autonomic responses, which may contribute to the treatment of a number of disorders, such as orthostatic intolerance in aerospace crews, assist in the alleviation of cardiac arrhythmias and hypertension, and as an alternative treatment to pharmacological management for alleviating space motion sickness (SMS) in astronauts and cosmonauts.
5. Training people suffering from migraine or tension headaches to control peripheral blood flow and reduce forehead and/or trapezius muscle tension.
6. Training elderly people suffering from fecal incontinence to control their sphincter muscles.
7. Training cancer patients to reduce the nauseagenic effects of chemotherapy.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION OF THE INVENTION

Figure 1:
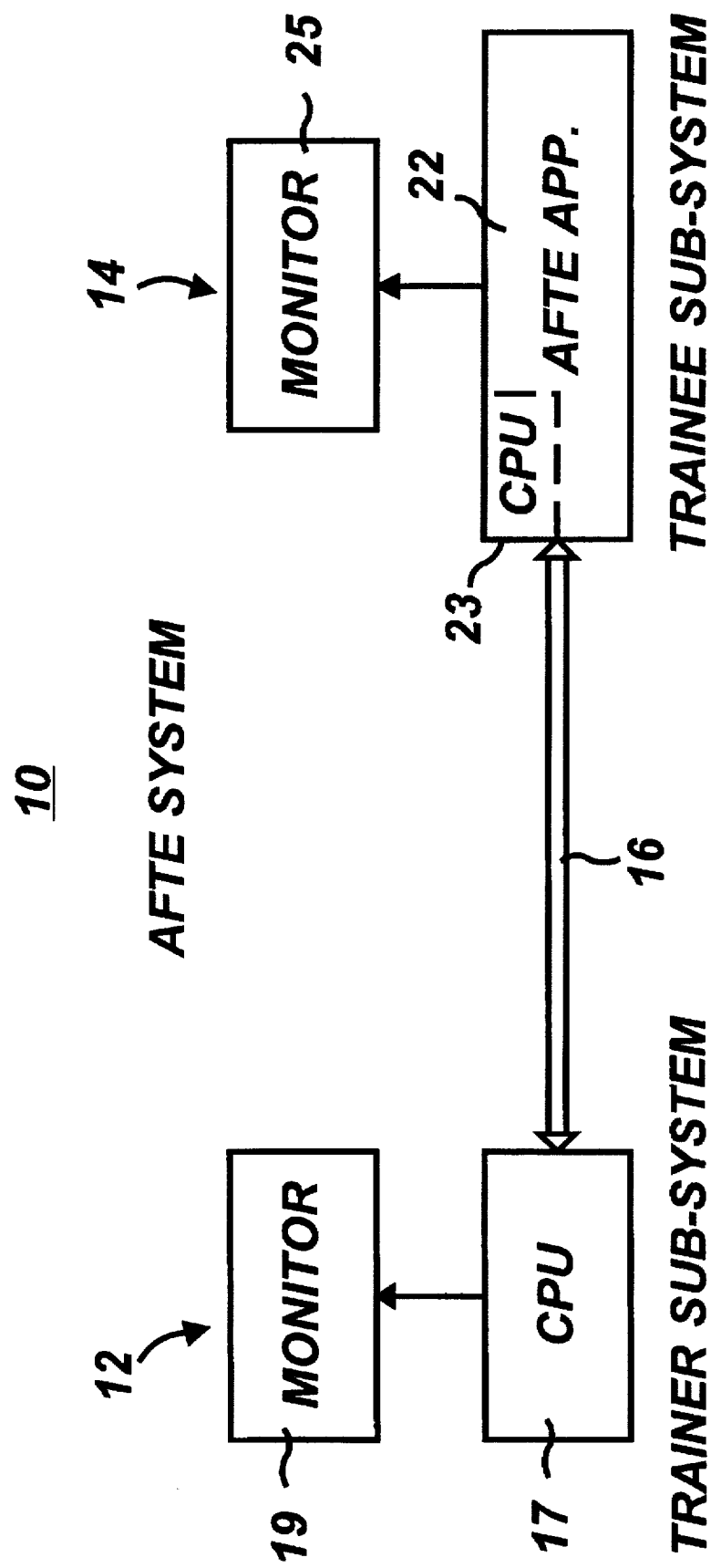
FIG. 1 represents a high level block diagram of an AFTE system according to the present invention.

The present autogenic-feedback training exercise (AFTE) system 10 of the present invention is generally illustrated in FIG. 1 and includes a trainer sub-system 12 and a trainee sub-system 14 that are interconnected by means of a data bus 16. The trainer sub-system 12 includes a CPU or personal computer (PC) 17 connected to a monitor 19. The trainee sub-system 14 includes an AFTE apparatus 22 which is connected to a monitor 25. The AFTE apparatus 22 may include a CPU or personal computer 23 and a wrist display 30.

A trainer monitors a trainee's physiological parameters and, pursuant to an AFTE method to be described later, selectively feeds back some or all of these parameters to the trainee for display on the monitor 25. The trainer's CPU 17 stores the baseline values and the voluntary changes in the trainee's physiological parameters during the training sessions. These values and changes may be downloaded to, and stored in the CPU 23 for reference and processing, when the trainee uses the AFTE apparatus 22, in real life situations. In one embodiment, the CPU 23 "learns" that particular trainee's own physiological and behavioral responses.

The present AFTE method shows a SNS activation in response to a stress-inducing stimulus, such as motion sickness stimulation, and proposes that motion sickness can be categorized as a stress response. When an individual is exposed to stress, such as motion sickness-inducing stimuli, he/she responds with an integrated pattern of somatic, sensory, and visceral activity. This pattern of measurable behaviors, referred to as a stress profile, can be defined as observed changes in the magnitude, latency, and phase relationships of those physiological responses which diverge from baseline following stimulation. No two individuals produce precisely the same stress profiles. Some individuals may show maximal responses in one or more organ systems while showing no significant change in another system. Although response magnitudes or latencies of the physiological profile of an individual may differ when stimulus conditions are changed, the basic underlying pattern remains highly idiosyncratic.

Because the physiological and behavioral responses are time dependent, examining a stress profile involves defining the signal which represents a specific biological process (e.g., heart rate) and delineating both its tonic and phasic properties. Tonic activity is the underlying baseline level which is relatively stable over time. By contrast, phasic activity refers to transient responses superimposed on the tonic level. Before the complete topography of a stress profile of a trainee can emerge, it is important not only to define the characteristics of each single response, but also the sequential patterning (or phase relationships) of several variables over time. The trainee is given a motion sickness test and his/her individual stress profile is recorded. The trainee is then trained, using the present AFTE method and AFTE apparatus 22, to simulate his/her own baseline levels during subsequent motion sickness tests.

The AFTE method includes several processes: (1) The baseline or pre-training process; (2) the training process; and (3) the post-training process. Each of these processes will now be described.

During the baseline or pre-training process, the trainee is seated in a motor powered rotating chair which is used to provoke the symptoms of motion sickness. The rotating chair is located in a soundproof room, and is capable of both clockwise and counterclockwise rotation, with speeds ranging from 6 rpm to 30 rpm. The trainer and the trainer's sub-system 12 are located out of the trainee's sight in an adjacent room, with audio and data communication between the trainer and the trainee being exchanged via the data bus 16. Some steps of the AFTE pre-training process are described in Stout, C. S., Toscano, W. B., Cowings, P. S., "Reliability of Psychophysiological Responses Across Multiple Motion Sickness Stimulation Tests", Journal of Vestibular Research, Vol. 5, No. 1, pages 25–33 (1995).

The trainee is connected to the AFTE apparatus 22 to enable the simultaneous monitoring of multiple physiological responses. The AFTE apparatus 22 is a lightweight, self-contained, battery-powered, ambulatory, physiological-monitoring apparatus. It can continuously and simultaneously monitor, display, and record several (e.g., five) channels of physiological parameters or functions for an extended period of time.

Figure 2:
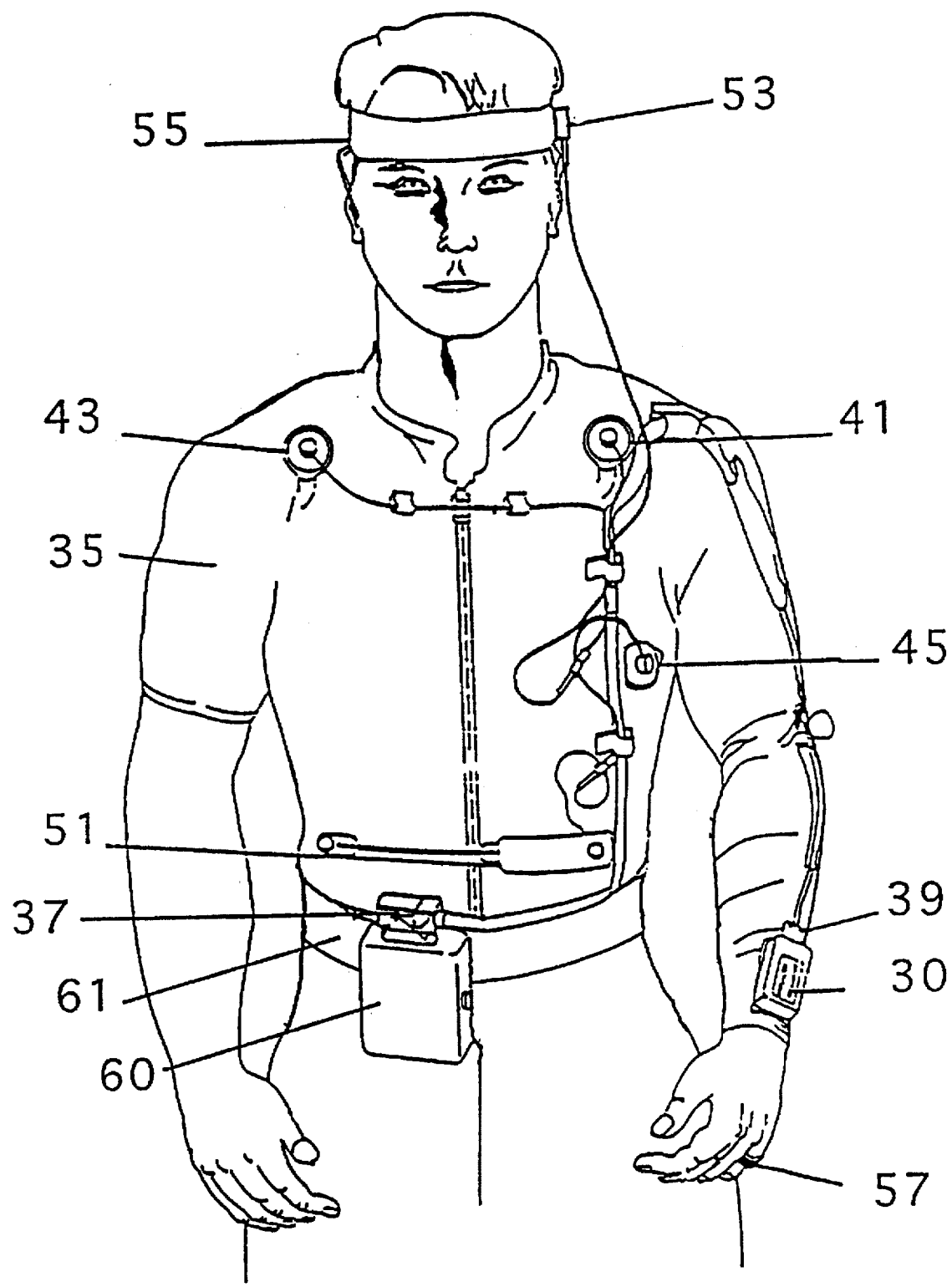
FIG. 2 illustrates a first embodiment of an AFTE apparatus that forms part of the AFTE system of FIG. 1, shown in use by a trainee.
Figure 3:
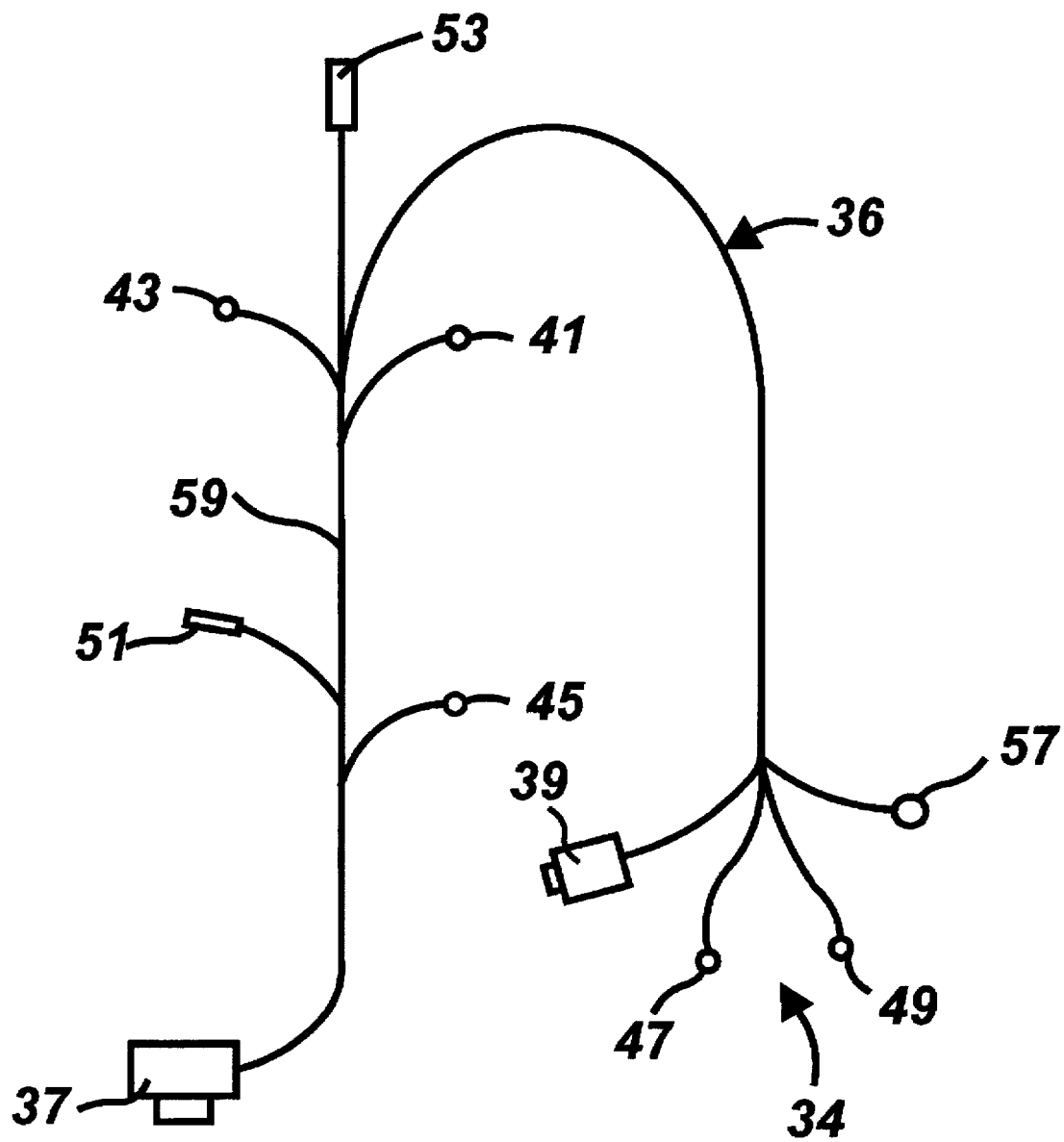
FIG. 3 is a representation of a sensor assembly and a cable assembly forming part of the AFTE apparatus of FIG. 2.
Figure 4:
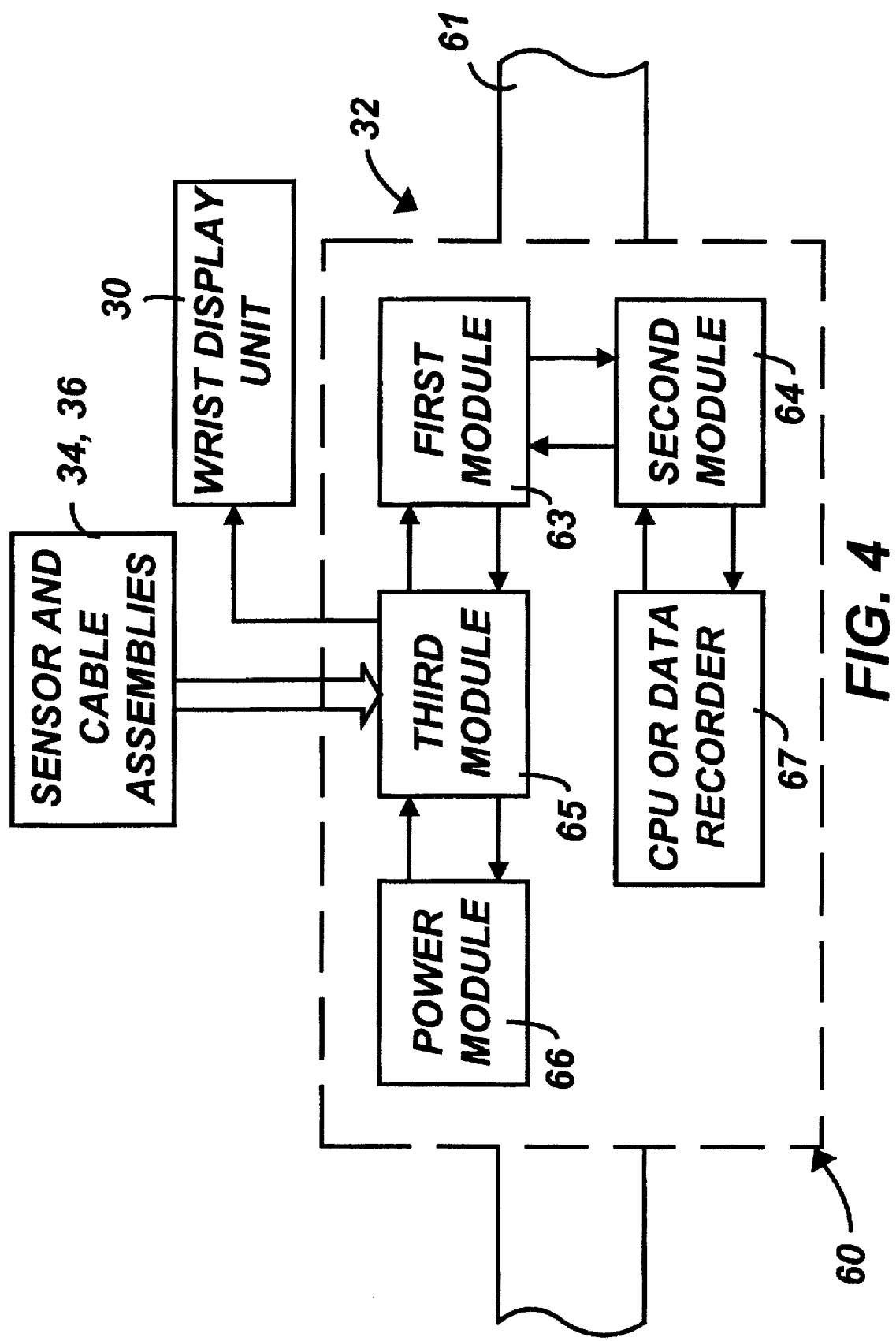
FIG. 4 is high level block diagram of a belt assembly forming part of the AFTE apparatus of FIG. 2.

A first exemplary embodiment of the AFTE apparatus 22 worn by a trainee, is illustrated in FIG. 2, and more detailed block diagram illustration of the AFTE apparatus 22 is shown in FIG. 4. The AFTE apparatus 22 generally includes the wrist display unit 30 which can provide an analogue or a digital numerical display of the trainee's physiological parameters; a belt assembly 32 which generally includes the system electronic circuitry and power supply; a sensor assembly 34 which includes a plurality of sensors and transducers that are placed on various locations on the trainee's body; and a cable assembly 36 for electrically interconnecting the various components of the AFTE apparatus 22, and for further connecting the AFTE apparatus 22 to the CPU 23. The sensor assembly 34 and the cable assembly 36 are further illustrated in FIG. 3, and can be secured to a specially tailored garment 35 for convenient donning.

The wrist display unit 30 selectively displays real-time physiological data, and also provides system malfunctions and low power (i.e., battery) indications. It may be worn on the trainee's wrist. During the pretraining, training, and post training sessions, the wrist display unit 30 may be activated. Some of the most common physiological parameters to be displayed by the display unit 30, either simultaneously or separately are: blood volume pulse (BVP)/skin temperature, heart rate, skin conductance level, and respiration rate.

The physiological data is collected by means of the sensor assembly 34, and transmitted to the wrist display unit 30, the CPU's 17, 23, and the monitors 19, 25, by means of the cable assembly 36 and the data bus 16. FIG. 3 illustrates an exemplary sensor assembly 34 whose components are interconnected by means of the cable assembly 36.

The cable assembly 36 carries signals from the trainee's body to the belt assembly 32 and includes a connector 37 for connection to the belt assembly 32. The cable assembly 36 carries signals from the belt assembly 32 to the wrist display unit 30, and includes a connector 39 for connection to the wrist display unit 30.

The sensor assembly 34 includes a plurality of sensors and transducers for sensing the trainee's various physiological parameters. While only a few of these sensors and transducers will now be described, it should be understood that additional or alternative sensors may also be used.

The present sensor assembly 34 includes three color coded ECG electrode snaps 41, 43, 45 for connection to three corresponding ECG electrodes (not shown) placed on the trainee's body. For instance, a white snap 43 connects to the electrode placed on the right chest region; a green snap 41 connects to the electrode placed on the left chest region; and a black snap 45 connects to the electrode placed below the left rib cage. In general, the ECG electrodes include three pregelled Ag/AgCl disposable electrodes that are placed on the chest just below the left and right clavicles (distally), and on the left mid clavicular line over the fourth intercostal space. These ECG electrodes monitor the trainee's cardiac electrical impulses. Other electrodes positioning is also possible.

The sensor assembly 34 further includes two skin conductance level (SCL) electrode snaps 47, 49 that are connected to two SCL electrodes placed on the trainee's wrist, or attached to the tips of the right index and middle fingers. The SCL electrodes monitor changes in the electrical conductivity properties of the skin, and include two pregelled Ag/AgCl disposable electrodes that are mounted on the volar surface of the left wrist and spaced 1 inch apart to measure the conductivity of the skin produced by moisture from the sweat glands.

Additionally, the sensor assembly 34 includes a respiration transducer 51 for connection below the chest, in order to detect changes in thoracic cavity size caused by the expansion and contraction of of the diaphragm. The respiration transducer 51 measures both the range and frequency of respiration (i.e., respiratory waveform), and converts this measurement to a DC voltage, and transmits the information to the belt assembly 32. The respiration transducer 51 includes a metallized kynar piezovoltaic transducer element configured as a load cell, sandwiched between two strips of silicone-rubber tape. A piece of medical grade Silastic™ tubing is used as a spring to transfer a force to the load cell proportional to the abdominal circumference changes.

A triaxial accelerometer 53 forms part of the sensor assembly 34. It measures gross head movements in three directions, and transmits this data to the belt assembly 32. The accelerometer 53 may be worn on the trainee's head either with a fabric headband 55 or with a communication headset. The accelerometer 53 includes three, half-bridge accelerometers mounted on a printed circuit board with trimming resistors.

A ring transducer 57 measures skin temperature and detects blood volume pulse (photoplethysmography or PPG), such as finger pulse volume. It may be worn on the fourth or little finger of the trainee's hand. The ring transducer 57 includes a solid state temperature transducer, for measuring skin temperature, and an infra-red photo emitter/detector pair, for detecting blood volume pulse (photoplethysmography).

Other sensors may also be used to measure and sense physiological parameters. Some of these physiological parameters and corresponding sensors are;

Blood Pressure (BP): BP measures will be used as primary feedback parameters to measure AFTE treatment effectiveness. A non-invasive system is used and includes two blood pressure cuffs mounted over the brachial arteries of the left and right arms. The cuff measuring systolic blood pressure will be initially inflated to just above systole. Using the R wave of an electrocardiogram to initiate a timing window, cuff pressure is automatically deflated or inflated, in 3 mm Hg increments, as the system "searches" for the presence of Korotkoff sounds detected by a crystal microphone beneath the cuff. If the K-sound is present, cuff pressure is increased on the subsequent heart beat; if absent, cuff pressure will be decreased. In this manner, it is possible to track blood pressure on each heart beat. The tracking cuff will be inflated for a period of 90 seconds at a time, alternating with deflation during 30-second "rest periods" to allow normal circulation to resume. The measurement of diastolic blood pressure (on the other arm) reverses this process.

Impedance Cardiography (I-C): A disposable aluminized mylar strip electrode tape is used to obtain this measure. Two strips of the electrode tape are placed around the trainee's throat (3 cm apart). Two additional strips are placed around the trainee's upper and lower thorax. Changes in transthoracic electrical impedance, which fluctuates with the phase of the heart cycle, will be recorded. This measure provides a reliable index of (a) stroke volume, (b) contractility, (c) cardiac output, and (d) systolic timing intervals. It may also be possible to directly train subjects to control central blood volume. The effects of AFTE on these indices of cardiovascular function will be documented. Possible mechanisms for AFTE effects may be deduced by observing effects on variables innervated only by sympathetic pathways.

Impedance Plethysmography (I-P): Lower limb volume will be monitored and displayed to trainees as a feedback to determine the extent to which this response may be directly conditioned and/or changes in limb volume resulting after control of blood pressure has been established. Two mylar strips of electrode tape are wrapped abound the trainee's ankle and just above and below the knee.

Electromyography of leg and forearm muscles (EMG): muscle activity of the legs will be monitored and physiological feedback provided. The degree of muscle involvement in learning control of blood pressure will be documented. Muscle activity of both forearm extensors and both gastrocnemius (back of calf) muscles will be measured. At each location, EMG will be measured with three silver—silver pregelled disposable electrodes.

Electroencephalography (EEG): Brain electrical potentials will be monitored at four scalp surface locations: left and right mid-temporal, mid-frontal and mid-occipital. An electrolyte gel will be applied to each silver—silver chloride electrode and they will be secured with the elastic head band 55.

Electro-oculography (EOG): Eye movements will be measured with two pairs of pre-gelled self-adhesive electrodes. One pair of electrodes will be placed near the left eye on the supra- and infra-orbital sites, and the second pair will be placed on the left and right external canthi.

Electrogastrography (EGG): Gastrointestinal smooth muscle surface potentials will be recorded from cutaneous silver—silver electrodes. Four pairs of electrodes will be positioned vertically over the abdomen, approximately 5 cm between each pair. The first pair will be centered at the intersection of the left mid-clavicular line and the costal border. The second pair will be centered approximately 3 cm left of the umbilicus. The third pair will be centered approximately 4 cm to the right of the umbilicus, and the fourth pair will be centered approximately 10 cm to the right of the umbilicus. These bipolar electrodes will be connected to a battery operated differential amplifier.

The cable assembly 36 includes a cable harness 59 made of biomedical grade, silicone-jacketed cables and PVC-jacketed electrode snap-leads largely enclosed in a sheath. All of the silicone-jacketed cables have internal shields and Teflon® insulated wire. The total length of the cable harness 59 depends on the trainee's body size.

Referring to FIG. 4, the belt assembly 32 includes a modular package 60 and a belt 61. The modular package 60 houses the system electronic circuitry, a CPU with memory or a data recorder, and a system power supply. The modular package 60 is comprised of several interconnectable modules 63, 64, 65, 66, 67. For instance, a first module or analogue box 63 contains electronic circuits for an analog subsystem that provides signal conditioning for electrocardiogram, skin conductance level, temperature, blood volume pulse, and respiration signals.

A second module or digital box 64 contains circuitry for a digital sub-system that:
1. Processes physiological signals in real-time for data feedback on the wrist display unit 30.
2. Times AFTE sessions.
3. Generates time and event codes.
4. Multiplexes time and event codes with temperature data.
5. Transmits a periodic time marker to the data recorder.
6. Interfaces with diagnostic equipment and the CPU 23.
7. Configures the system operating modes.
8. Amplifies the signals from the accelerometer 53.

A third module or junction box 65 collects system inputs from the sensor assembly 34, and from the power source, i.e., the battery pack, and relays these inputs to the first and second modules. The third module 65 also generates different voltages not provided by the power source, with special power conditioning circuitry, and provides short circuit protection circuitry for the accelerometer 53 and the wrist display unit 30.

A fourth module 66 consists of the battery pack that supplies power to the entire AFTE apparatus 22. The battery pack includes four conventional 9V transistor type batteries.

A fifth module 67 includes the CPU 23 and/or a data recorder. The data recorder receives PPG waveform, skin temperature, skin conductance, respiration waveform, ECG waveform, acceleration signals, time and date, specified events, and session timing data and records them onto a standard-sized magnetic data instrumentation cassette tape. Alternatively, this information may be stored in the CPU (23) memory.

The wrist display unit 30 indicates when Blood Volume Pulse (BVP) is active. A heart shaped symbol will flash each time the AFTE apparatus 22 detects a pulse on the BVP waveform. The trainee may use the BVP indicator to position the ring transducer 57 properly, or to cross-check the validity of the numerical BVP display by comparing the flashing heart symbol with the heart beats detected manually. In this particular example, the flashing heart is derived from the BVP waveform and not from the ECG signal. The wrist display unit 30 also displays the Blood Volume Pulse amplitude in relative numbers.

The wrist display unit 30 indicates when the accelerometer 53 malfunctions or exceeds its measurement range. Three independent accelerometer functional indicators "X", "Y", and "Z", show that the accelerometer 53 is functioning and indicate any errors detected by the AFTE apparatus 22. Each individual indicator is dedicated to respond to its own respective axis. Each corresponding accelerometer functional indicator will remain "off" when its respective accelerometer is within measurement range, and will turn "on" when the signal exceeds the measurement range. The indicator will remain on steadily when the AFTE apparatus 22 has detected an error with the accelerometer 52 (i.e., when the accelerometer is disconnected). Under normal conditions, the accelerometer functional indicator will flash on and off as the accelerometer 53 is moved.

The wrist display unit 30 displays the heart rate in numbers of beats per minute, and the respiration rate in breaths per minute. It measures the AFTE sessions, which may be 15 minutes long segmented into five three-minute intervals. During each interval, the trainee performs certain exercises, depending upon the particular requirements of the training. Each interval is displayed on the wrist display unit 30 and time-marked on the data recorder with an event code. The wrist display unit 30 also displays the skin conductance level in relative numbers, and further displays an error signal when a malfunction occurs.

The wrist display unit 30 allows the trainee to select the display of Blood Volume Pulse in relative numbers, or skin temperature in degrees Fahrenheit. These two display parameters share the same data field, but are not displayed concurrently. The wrist display unit 30 also shows the current time and date.

The following TABLES I, II and III, summarize the operational specifications, the data channel specifications, and the wrist display parameters, respectively:

TABLE I

OPERATIONAL SPECIFICATIONS

| SPECIFICATION | RANGE |
|---|---|
| Operating Temperature | 17° C.–28° C. |
| Storage Temperature Range | 5° C.–50° C. |
| Humidity (Spacelab Ambient) | 25%–70% |
| Power (System) | 9 V/95 mA |
| Power (SCL subsystem) | 9 V/8 mA |

TABLE II

AFTE DATA CHANNEL SPECIFICATIONS

| PARAMETER | RANGE | BANDPASS | ACCURACY |
|---|---|---|---|
| Electrocardiogram (ECG) | 40–180 bpm | 0.5–40 | N/A |
| Skin Conductance Level (SCL) | 50–0.5 µMHOs | DC–0.05 | ±2% |
| Respiration (RESP) | 4–60 brpm | 0.02–0.07 | N/A |
| Blood Volume Pulse (BVP) | 1–200 | 0.05–2.7 | 0.10% |
| Skin Temperature (TEMP) | 70–99.9° F | DC–0.1 | ±1° F. |
| X-Axis Acceleration | –0.25 to +0.25 G | 0.03–5.0 | ±5% |
| Y-Axis Acceleration | –0.25 to +0.25 G | 0.03–5.0 | ±5% |
| Z-Axis Acceleration | –0.25 to +0.25 G | 0.03–5.0 | ±5% |

TABLE III

WRIST DISPLAY PARAMETERS

| PARAMETER | UNITS | DIGITS | RANGE | RESOLUTION | ACCURACY |
|---|---|---|---|---|---|
| Heart Rate | bpm | 3 | 40–180 | 1.0 | ±0.5 |
| Skin Conductance Leve (SCL) | µMHOs | 4 | 50–0.50 | 0.01 | ±0.025 |
| Respiration Rate (RESP) | brpm | 2 | 4–60 | 1.0 | ±0.5 |
| Blood Volume Pulse (BVP) | Relative | 3 | 1–200 | 1.0 | ±0.5 |
| Temperature (TEMP) | °F. | 3 | 70–99.9 | 0.1 | ±1.0 |
| Time | GMT | HH:MM:SS (Not displayed Concurrently with other parameters) | | | |
| Malfunction Indicator | M1" | | | | |
| Low Battery Indicator | L | | | | |
| Acceleration X-Axis Over Range | X | | | | |
| Acceleration Y-Axis Over Range | Y | | | | |

TABLE III-continued

WRIST DISPLAY PARAMETERS

| PARAMETER | UNITS | DIGITS | RANGE | RESO-<br>LUTION | ACCU-<br>RACY |
|---|---|---|---|---|---|
| Acceleration Z-<br>Axis Over Range | Z | | | | |
| Blood Pulse<br>Indicator | ♥ | | | | |

Referring to FIG. 4, the signals are directed along two different paths from the second module 64. The first signal path moves to the CPU or data recorder module 67. The second signal path moves to the wrist display unit 30, via the first and third modules 63, 65 and the cable assembly 36.

Analog signals that are picked up from the ECG electrodes, SCL electrodes, ring transducer 57, respiration transducer 51, and the accelerometer 53 are routed to the CPU or data recorder module 67 for data storage, and to the second module 64 for display on the wrist display unit 30.

Figure 5:
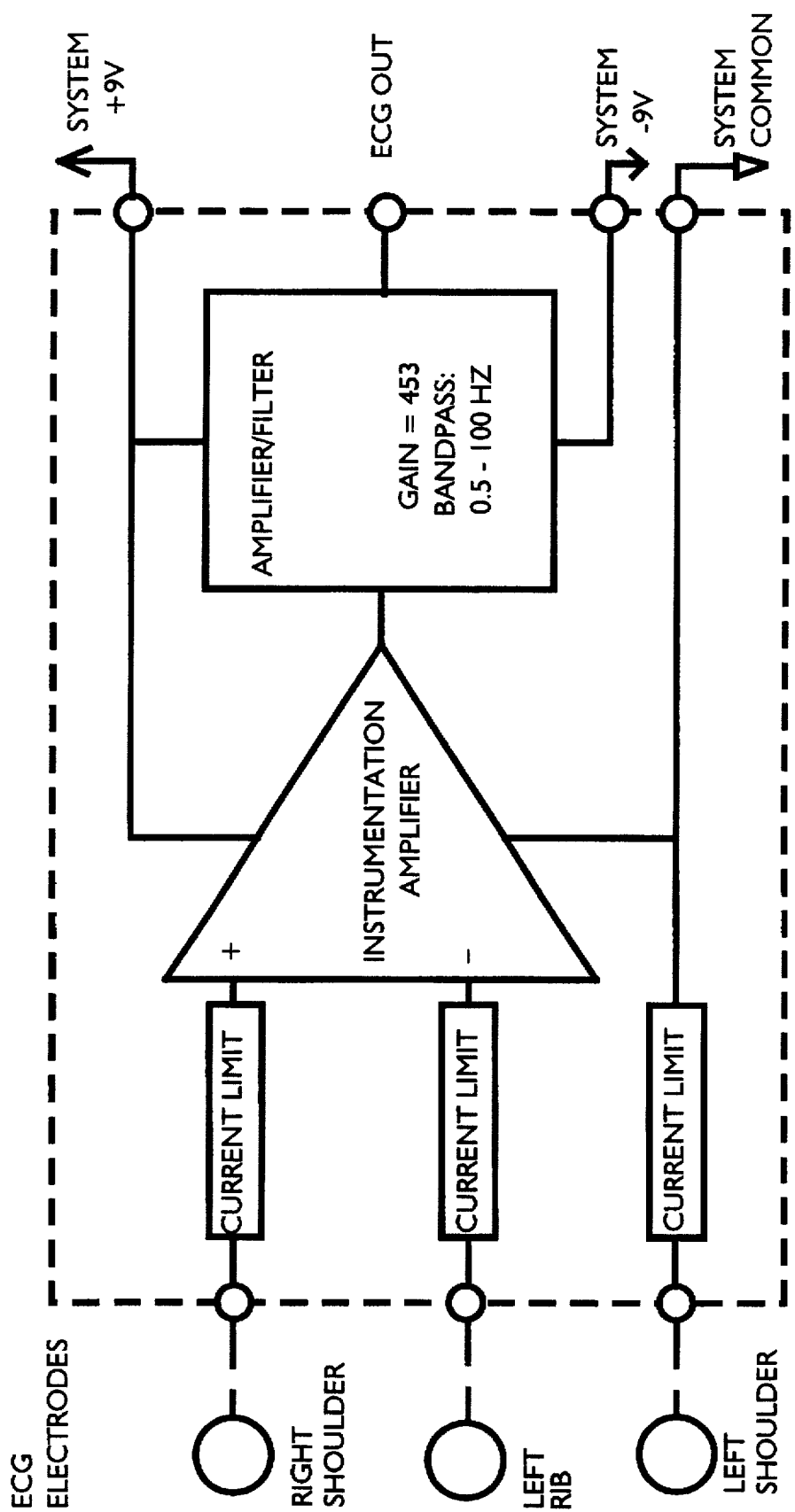
FIGS. 5 through 11 illustrate the diagrams of some of the electronic circuits forming part of the AFTE apparatus of FIGS. 2 and 4.
Figure 6:
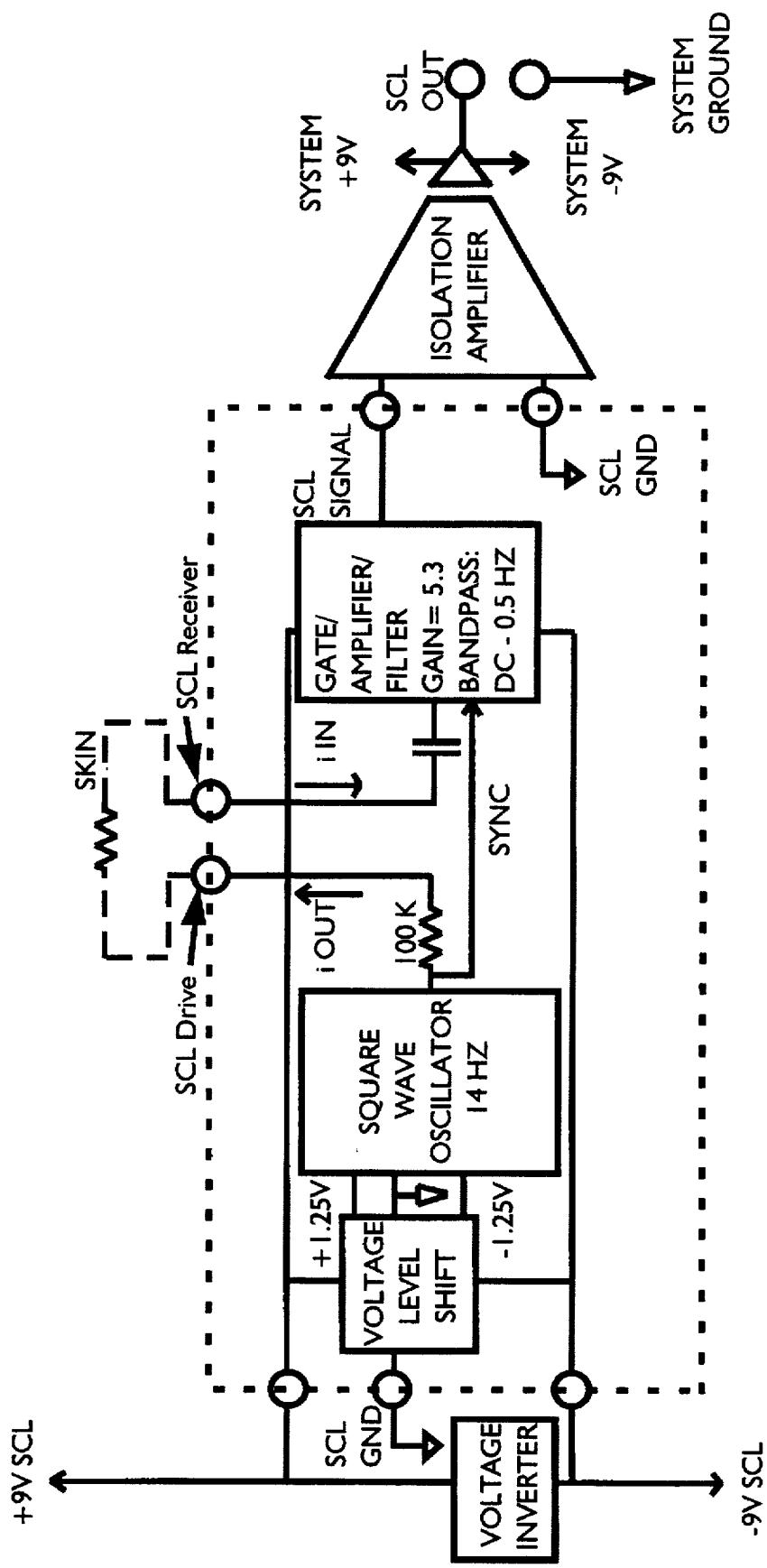
Figure 7:
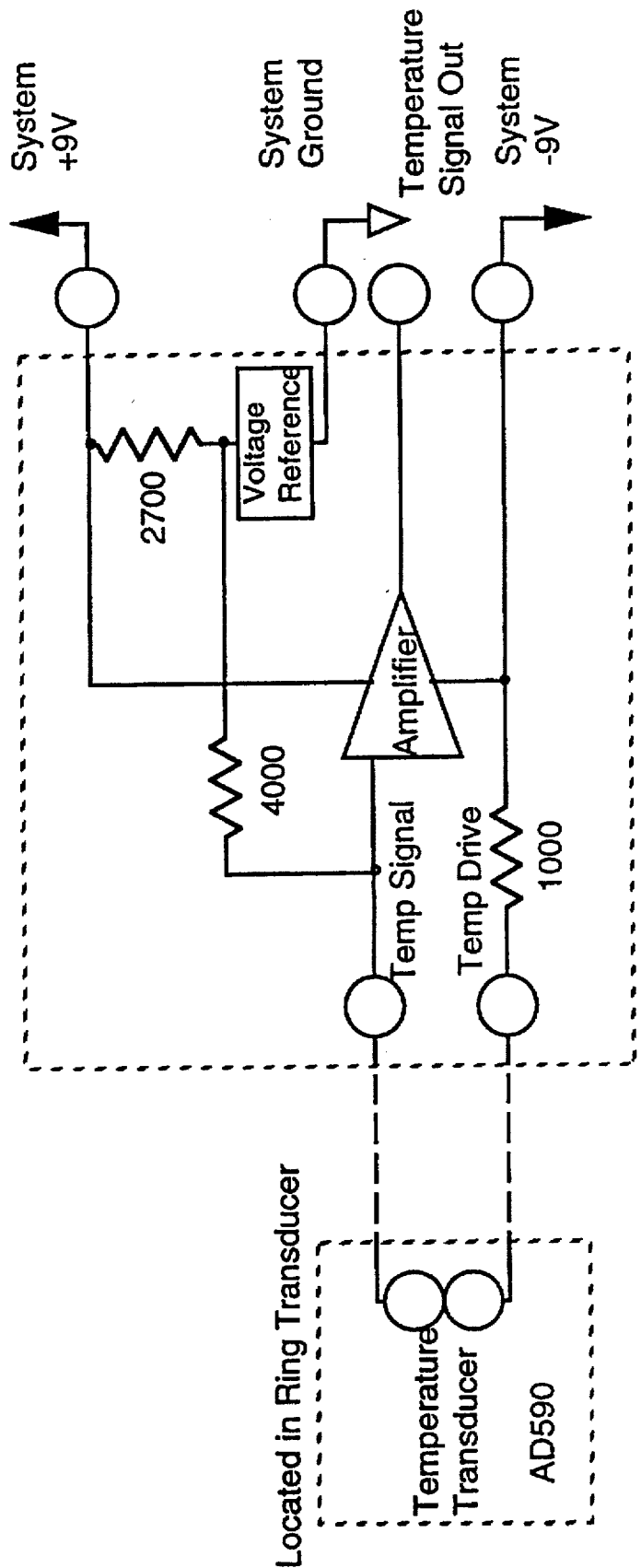
Figure 8:
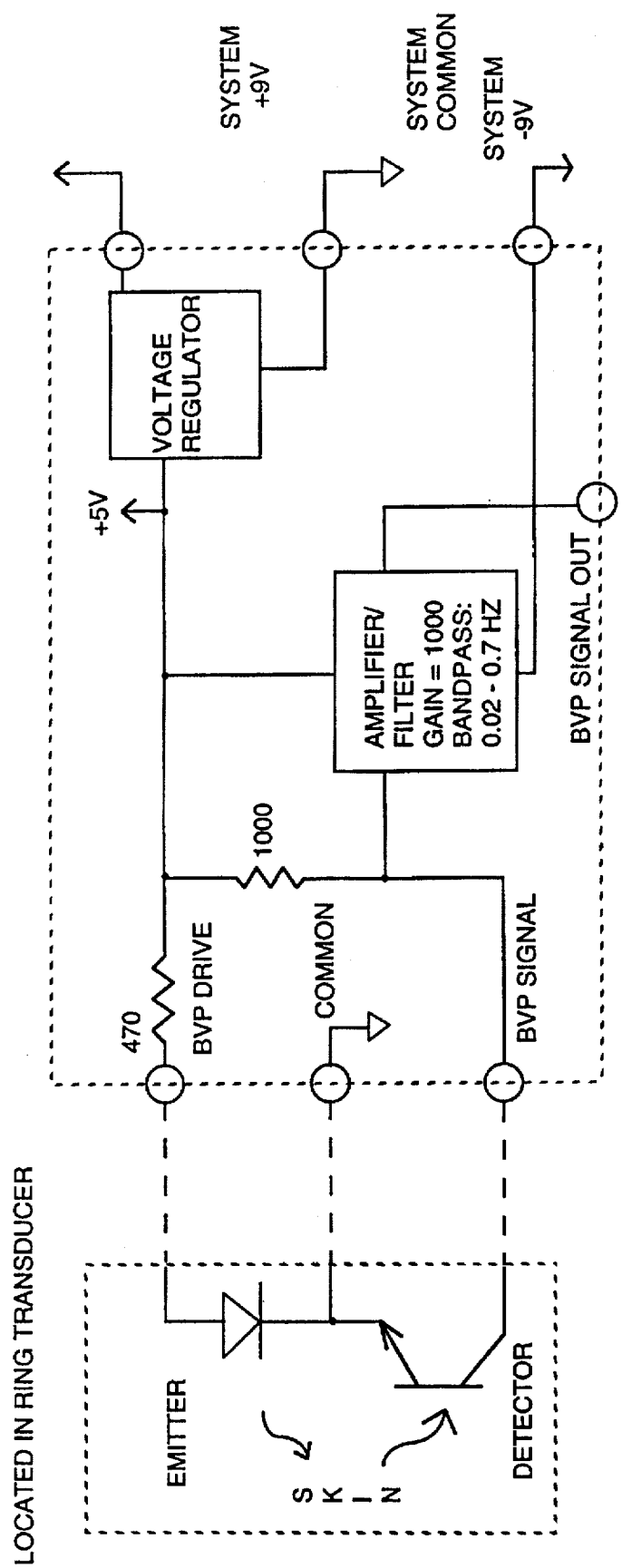
Figure 9:
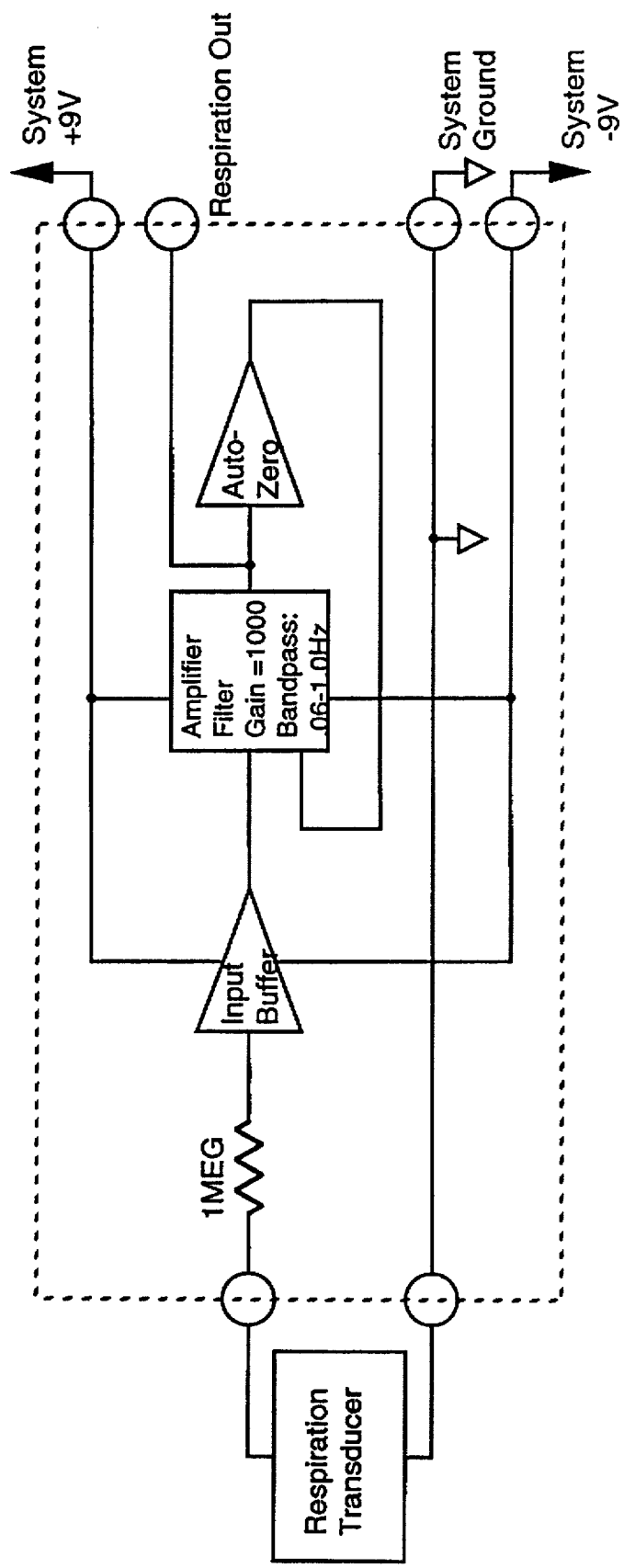
Figure 10:
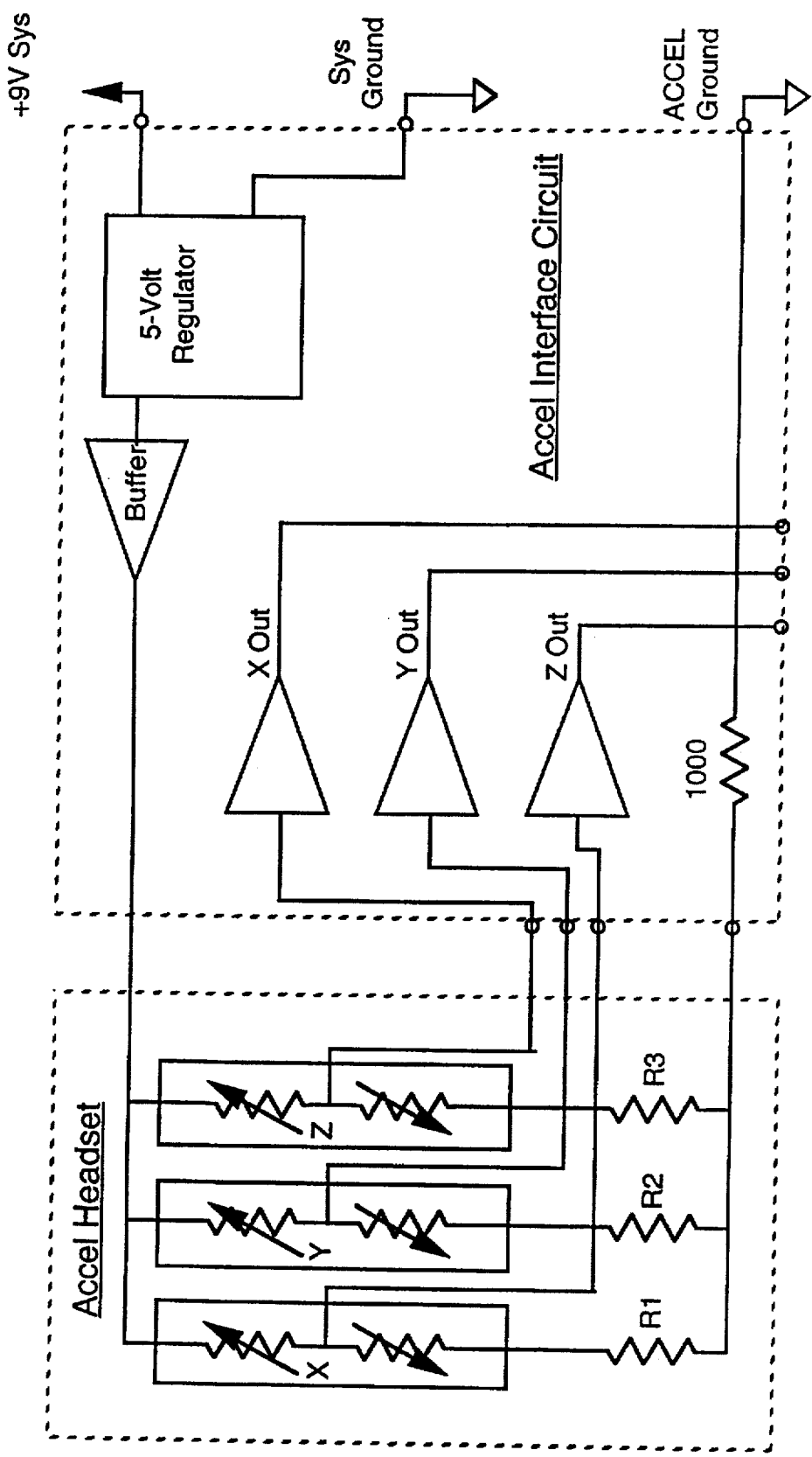
Figure 11:
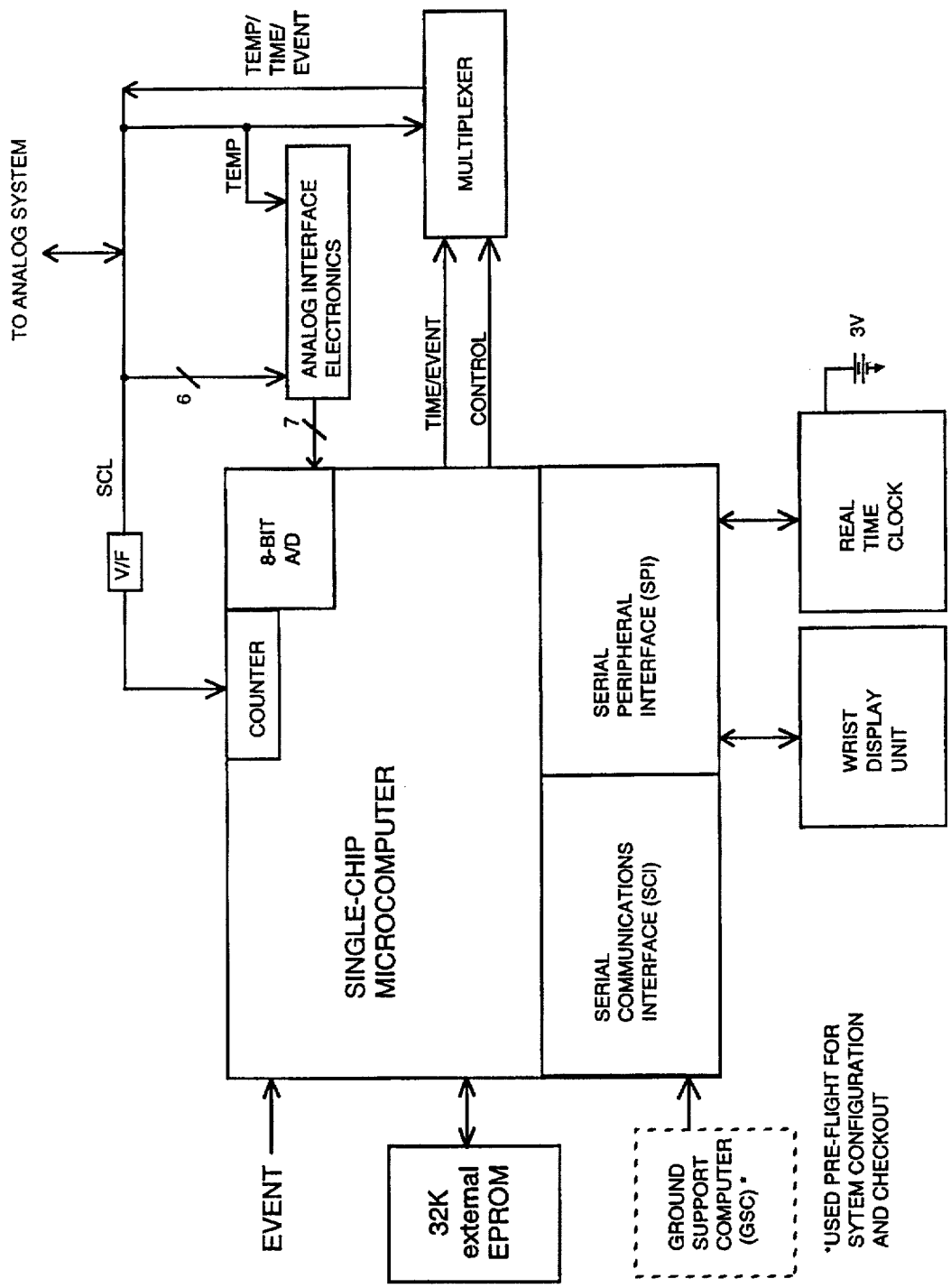

Referring now to FIGS. 5 through 11, they illustrate the diagrams of some of the circuits forming part of the AFTE apparatus 22. FIG. 5 represents an exemplary diagram of the ECG circuit. FIG. 6 represents an exemplary diagram of the skin conductance level circuit. FIG. 7 represents an exemplary diagram of the temperature circuit. FIG. 8 represents an exemplary diagram of the blood volume pulse circuit. FIG. 9 represents an exemplary block diagram of the respiration circuit. FIG. 10 represents an exemplary diagram of the accelerometer circuit. FIG. 11 represents an exemplary block diagram of the digital subsystem.

Returning now to the description of the baseline process, it includes the following stages:

1. Reduce the extrinsic stimuli, such as light and sound.
2. Determine the trainee's optimal range of physiological parameters at rest to obtain that trainee's individual baseline profile.
3. Familiarize the trainee with the AFTE system and method.
4. Gradually increase and then decrease the stimulus levels to determine the trainee's range of physiological parameters under stress, and the relationship of these parameters.
5. Determine which physiological parameters change the most, i.e., the order of change, under stress.
6. Determine the magnitude of response and the tonic and phasic relationship of the physiological parameters under stress.
7. Determine the developing symptoms and correlate them to accompanying changes in the physiological parameters.
8. Obtain the trainee's individual profile or specific response pattern under stress.
9. Train the trainee to use passive concentration.
10. Train the trainee to feel and pay attention to various bodily sensations.
11. Train the trainee to focus using passive attention.
12. Provide baseline test, starting with a specific autogenic exercise, such as respiration.
13. Repeat the baseline test until the trainee is ready to proceed with the training.
14. Train the trainee to normalize his/her individual profile and to modify his/her behavior, by providing bi-directional training (increase and decrease in response levels).
15. Store that individual stress profile in the CPU 17 and/or CPU 23.

The stored data may then be selectively downloaded to the CPU or data recorder module 67.

In order to determine the trainee's optimal range of physiological parameters at rest; and to obtain that trainee's individual baseline profile, the trainee is asked to sit in the chair and to relax. The trainer selectively performs one or more of the following six autogenic exercises:

1. Heaviness in the arms and legs.
2. Warmth in the periphery.
3. Regulated respiration.
4. Regulated heart beat.
5. Warmth in the solar plexus.
6. Coolness in the forehead.

The trainer begins with the respiration exercise, and simultaneously teaches the trainee to divide his/her attention. For instance a metronome is used to cause the trainee to synchronize the rate and depth of his/her breathing, while the trainer provides instructions in between the pitches of the metronome. Following the respiration exercise, the trainer proceeds with the heaviness exercise, followed by the warmth in the periphery exercise. The remaining exercises could be performed sequentially, if time permits.

The motor powered rotating chair is used to induce the initial symptoms of motion sickness. The trainee is seated in the chair and the center of rotation is through his/her own vertical axis (spine). Padded headrests are mounted on the sides, front, and back of the chair, which allows the blindfolded trainee to execute head movements in randomized directions at 45° angles from the upright position. Instructions for the head movement are provided by a tape recorded voice. Preamplifiers for physiological signals are mounted on the rear of the chair and the AFTE apparatus 22 is secured around the waist of the trainee. The amplified signals are sent through slip rings in the base of the chair to the trainer CPU 17. All physiological data are recorded on two 8 channel strip chart recorders and a fourteen track FM analog tape recorder, and are processed in real time and stored on the CPUs 17 and 23.

During each 5 minute interval throughout the motion sickness tests, the trainee is asked to report his/her symptoms to the trainer. The symptoms are graded using a standardized diagnostic scoring procedure.

The wrist display unit 30 and/or the monitor 25, provide the trainee with continuous numeric feedback of various physiological parameters that have been selected by the trainer. Some of these parameters are: heart rate, respiration rate, blood volume pulse, skin conductance, and skin temperature. Hardware malfunction indicators and time may also be provided to the trainee via the display 30 or monitor 25.

As a result of the gradual and alternating increase and decrease of the physiological response levels (bidirectional training), the trainer determines the trainee's range of physiological parameters under stress, and the relationship of these parameters. Specifically, the trainer determines which physiological parameters change the most, i.e., the order of change, the magnitude of response and the tonic and phasic relationship of the physiological parameters, as well as the developing symptoms. The trainer correlates these symptoms to accompanying changes in the physiological parameters, and the CPU 17 provides the trainee's individual profile or specific response pattern under stress. As a result, the AFTE method is tailored to the particular needs of each individual trainee.

Figure 12A:
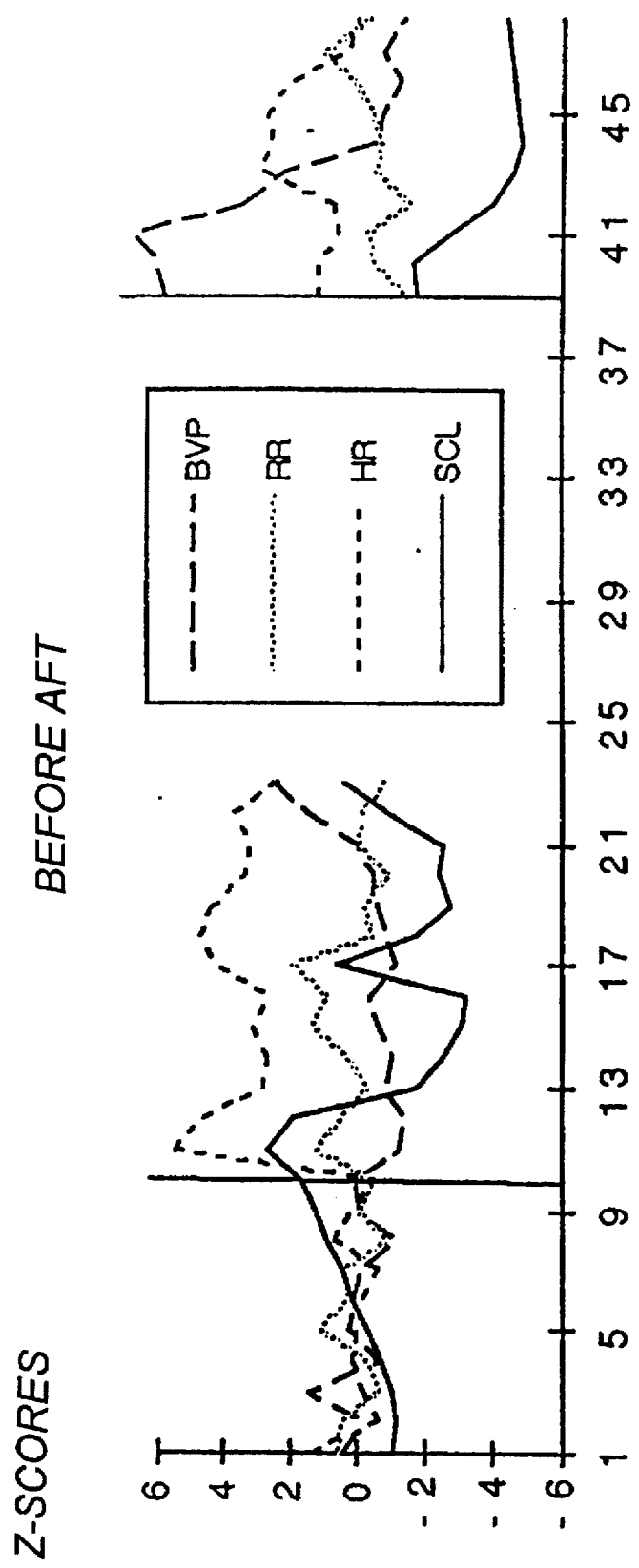
FIG. 12 represents a set of stress profiles of a first trainee during a rotating chair test.
Figure 13A:
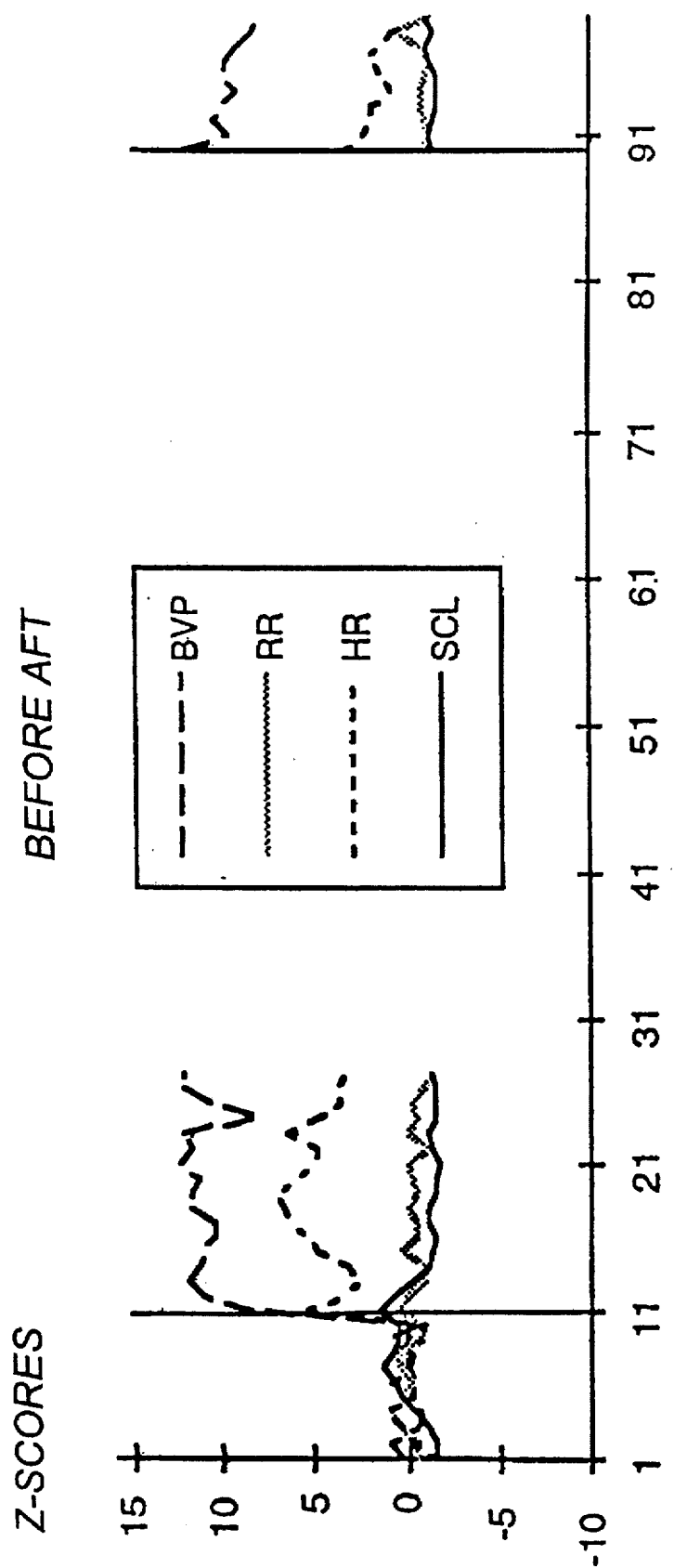
FIG. 13 represents a set of stress profiles of a second trainee during a rotating chair test.

FIGS. 12A and 13A show the stress profiles of two trainees during a rotating chair test. The first ten minutes illustrate the baseline physiological responses of the two trainees (at rest). Following this resting baseline, chair rotation is initiated at 6 rpm (0.628 rad/s) and incremented by 2 rpm (0.209 rad/s) every 5 minutes. The rotational velocity during each 5-minute interval is held constant. The maximum velocity is 30 rpm (3.136 rad/s). During each 5-minute period, the trainees execute 150 head movements in the four quadrants. Instructions for making head movements at 2-second intervals are delivered to the trainees by tape-recorded instruction. The direction of head movements is randomized. Following each 5-minute interval of rotation there is a 30-second pause (no head movements, but continued rotation) in which a standard diagnostic scale is administered. Prior to the start of the test, each trainee is instructed to attend to his/her symptoms and to report the symptoms during the 30-second pause. The trainees are asked to report any symptoms that occurred during the preceding 5 minutes. Tests are terminated at 30 rpm or at severe malaise, or whenever the trainees request to stop.

The diagnostic scale used to assess motion sickness symptoms is a standardized scale used to grade each trainee's level of malaise. This scale is based on self-report and the trainer's observation of several subjective symptoms such as body temperature, dizziness, headache, drowsiness, sweating, pallor, salivation, and nausea. To provide a measure of sickness severity in the trainees showing different symptom patterns, a single composite score is calculated for every 5 minutes of testing using a weighted scoring system. This composite score, or malaise score, ranges from 0 to 16.

The profiles illustrated in FIGS. 12A and 13A show that the physiological responses vary significantly with stress from one trainee to another, and that these responses are not normalized with the baseline responses once stress is applied.

Figure 12B:
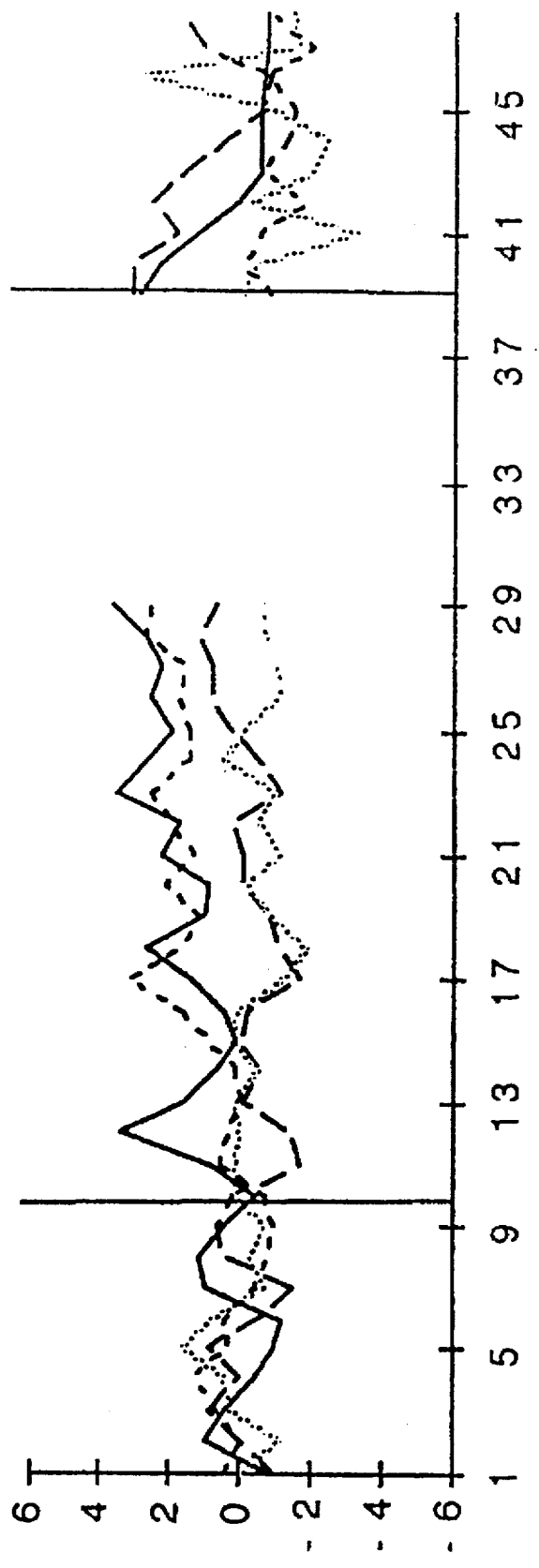
Figure 12C:
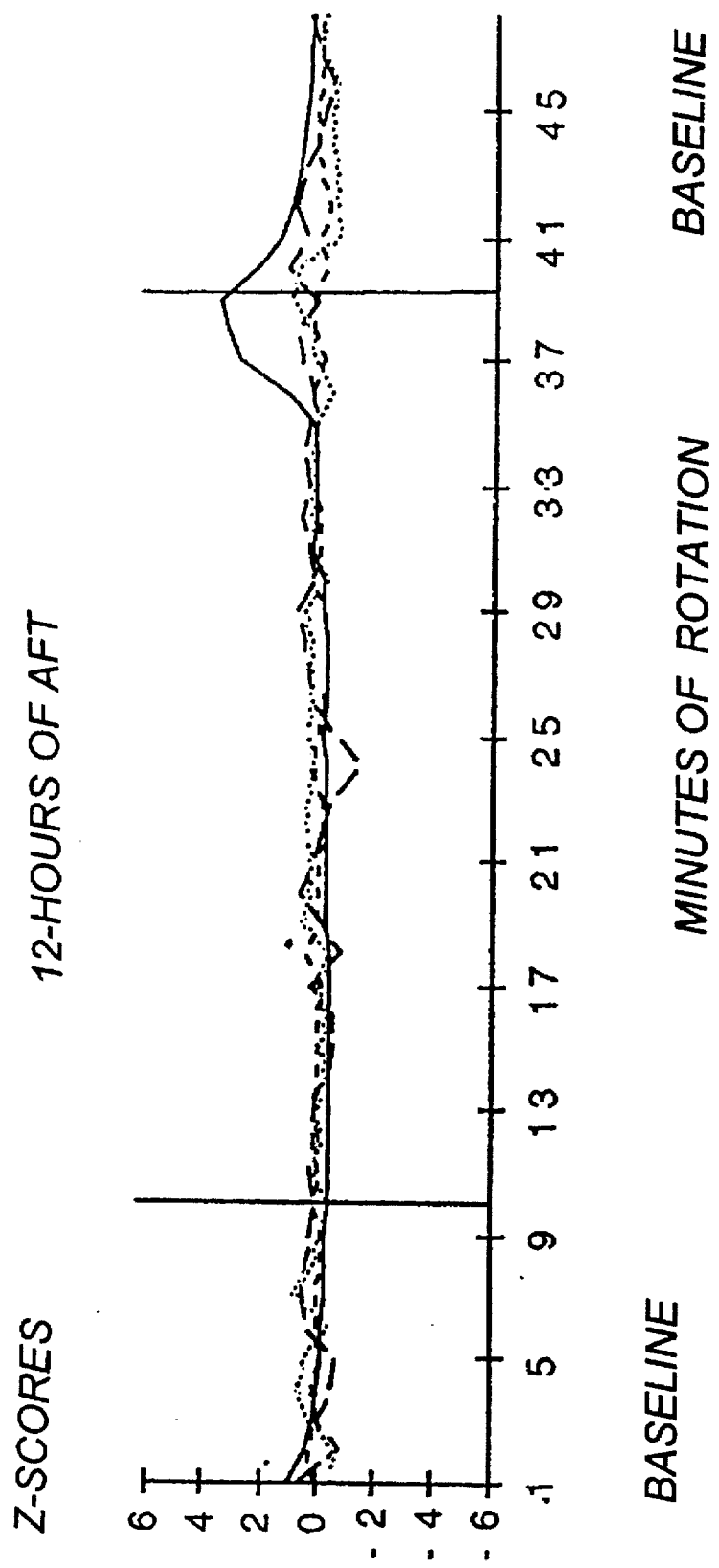
Figure 13B:
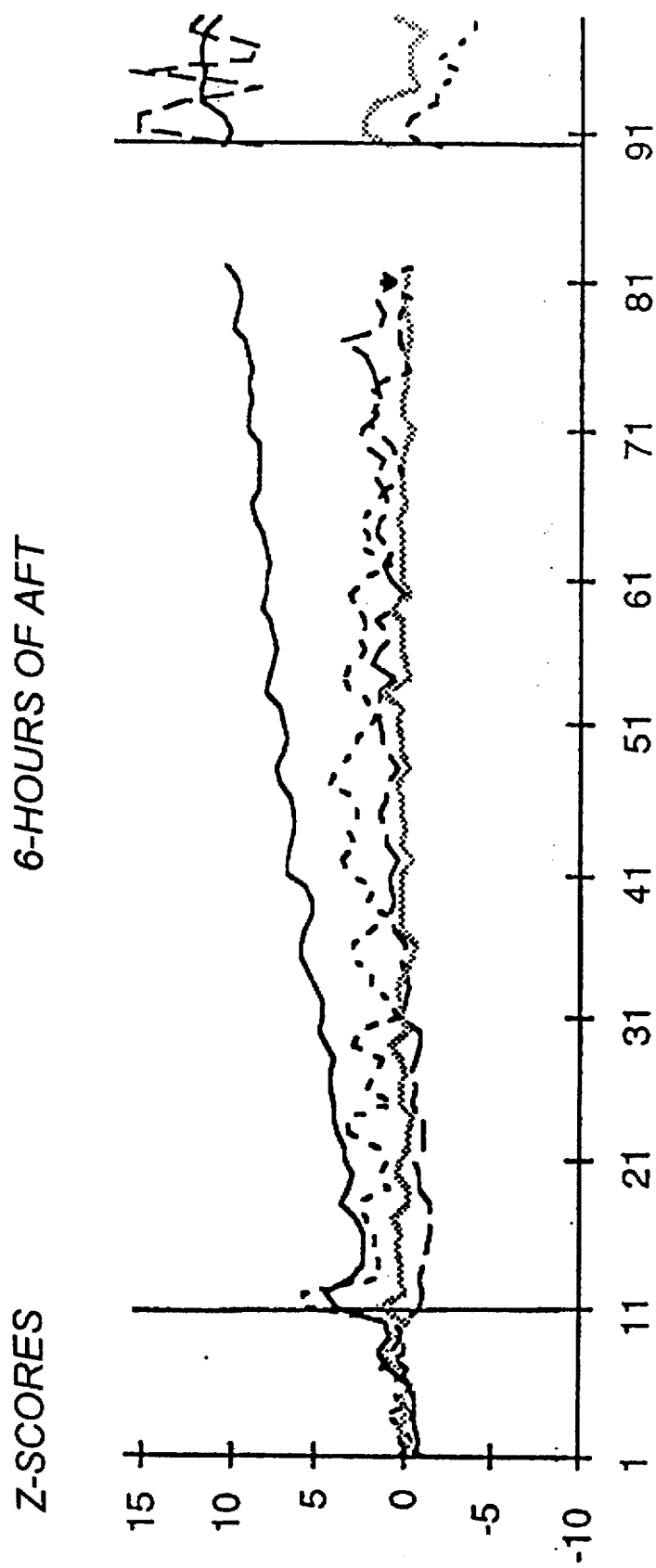
Figure 13C:
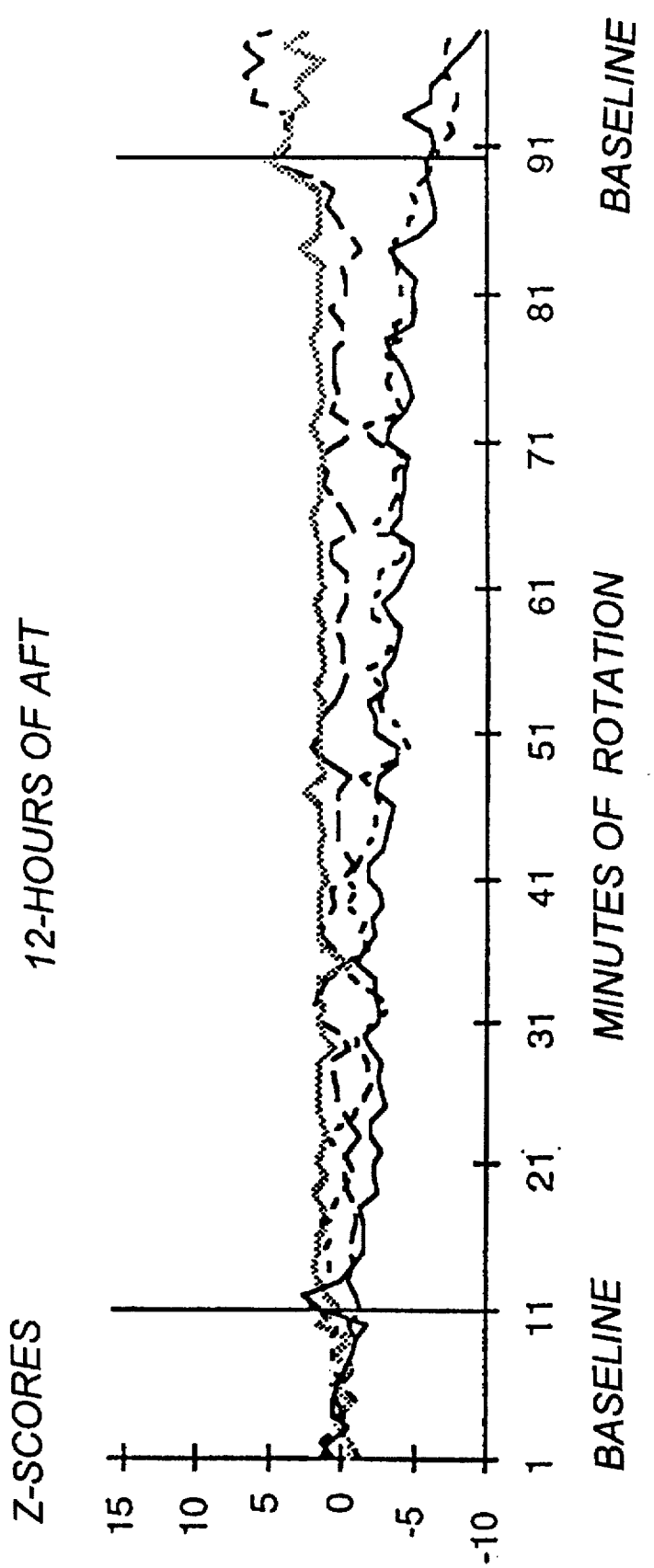
Figure 14:
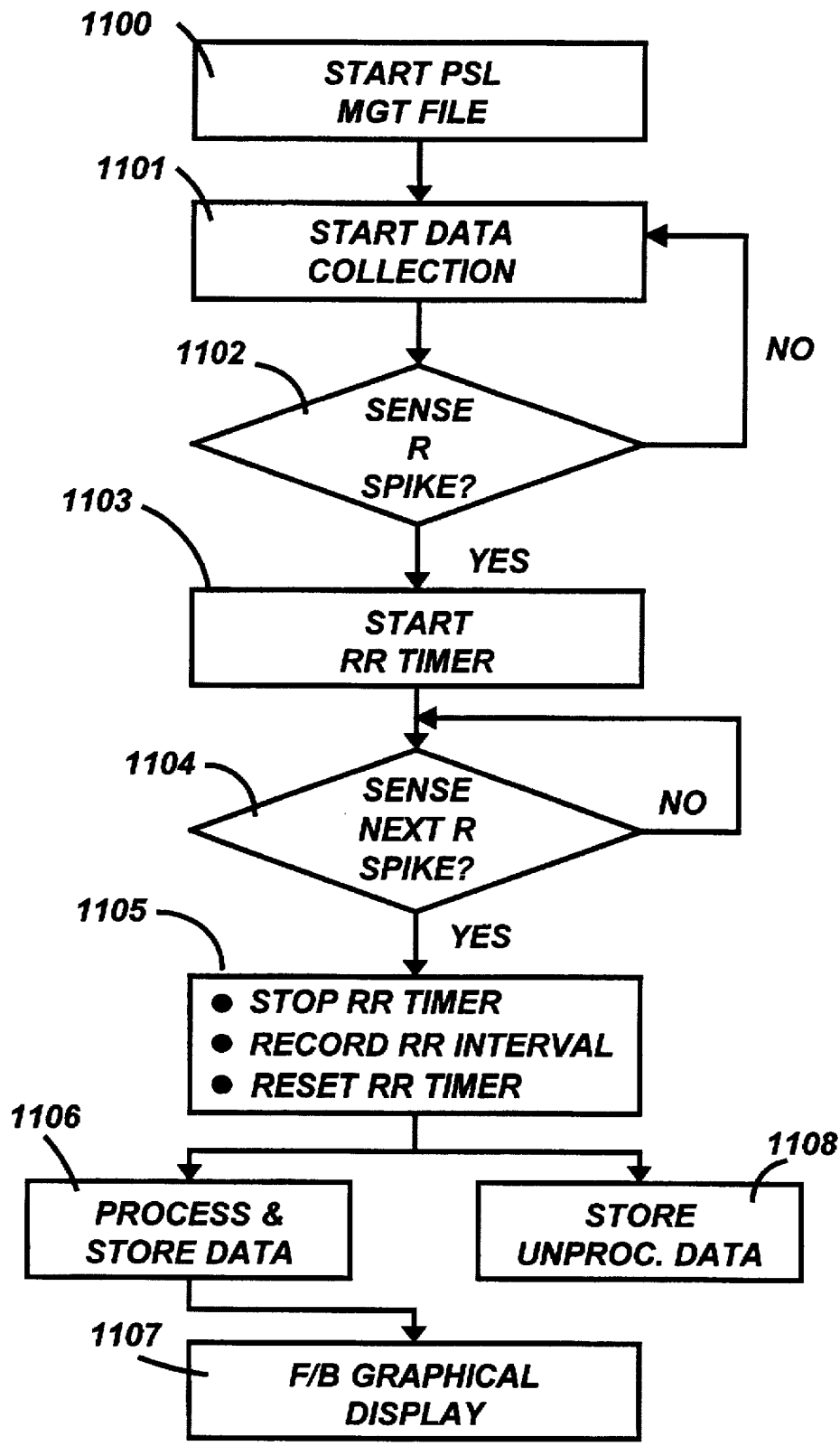
FIGS. 14 through 17 illustrate in a flow chart format, the operation of the AFTE system of FIG. 1.

One object of the present invention is to train the trainees to normalize their responses, as is shown in FIGS. 12C and 13C. For instance, the trainee is trained to simultaneously modify and control the hierarchy, magnitude and phase relationship of several physiological responses, aiming at keeping the levels of his/her physiological responses at, or close to baseline, under stress, in order to alleviate or prevent the developing symptoms. The AFTE method also aims at training the trainee to maintain normal regulation of the autonomic nervous system by maintaining balance between the two branches of the autonomic nervous system: the sympathetic and the parasympathetic branches.

Another observation from the stress profiles in FIGS. 12 and 13 is that the leading physiological response (i.e., the response that changes the most) also varies from one trainee to another. For instance, the leading physiological response in FIG. 12A is heart rate (HR), while the leading physiological response in FIG. 13A is blood volume pulse (BVP). These leading physiological responses identify to the trainer as well as the trainee which physiological response is likely to change most under stress, and emphasis is placed on training the trainee how to normalize this leading physiological response simultaneously with the other trailing physiological responses (i.e., that change less).

In this particular stress profile, the physiological responses measured are: blood volume pulse (BVP), respiration rate (RR), heart rate (HR), and skin conductance level (SCL).

The trainer trains the trainee to normalize his/her individual profile and to modify his/her behavior, by providing bi-directional training. It was proven that bidirectional conditioning, i.e., producing alternating increases and decreases in physiological responses, plays an important role in facilitating the transfer of learned autonomic control for the prevention of symptoms. Bidirectional training has proven to be effective because it teaches the trainee to recognize physical sensations associated with states of arousal and relaxation. The bidirectional training process will eventually provide the trainee with the ability to normalize his/her response levels during stressful conditions.

If the physiological responses exceed the optimal range during stress, an out of phase relationship develops between certain parameters, which provides an accurate indication or precursor, that certain symptoms will occur. During training, the trainee is made aware of certain body sensations like increased warmth in the hands and feet, and is trained to correlate this particular sensation with the onset of a specific symptom. The trainee is also trained to change his/her physiological responses or stress profile, to prevent or minimize the occurrence of the associated symptom.

During the baseline process, the trainer learns the trainee's behavioral and symptomatic changes, and the trainee learns about, and becomes conscious of his/her own behavioral pattern.

Stability of stress profiles from the motion sickness tests are demonstrated statistically as follows. The value of the variance components across five motion sickness tests is determined by an analysis of variance from the final minute of each autonomic response and final malaise score for each test. The statistical model relates the variance in the observed measure to variance between and variance within trainees. Second, using the obtained variances, the intraclass correlations (for one test), is estimated for the final minute of each physiological response and the final malaise level to assess within trainee reliability. To estimate reliabilities based on multiple test occasions (for two to five tests), the Spearman-Brown formula is applied. Intraclass correlations and reliability estimates pertain to the relative degree of consistency among sets of intraclass scores. In this case, the intraclass scores are represented by five different test occasions. The intraclass correlation and reliability estimates are each based on the number of test occasions. As more test occasions are included in the estimate, the reliability increases. An acceptable scientific standard is reliability $\geq 0.80$.

To examine the change in each autonomic response measure and malaise level over the entire duration of the motion sickness test, the trainer performs a linear regression analysis, with time as the independent variable. A separate analysis for each of five rotating chair tests on each physiological response and malaise score for each individual is performed. Baseline data, that is, resting autonomic activity levels without rotation, of all trainees, are collected for 10 minutes prior to each test. The trainer uses the average baseline physiological response from minutes 6 through 10 as the first data point in each trainee's analysis, and also uses 5-minute averages of physiological responses in the linear regression analyses for subsequent data points. These averages are used because malaise scores are recorded at discrete time intervals at the end of each 5-minute rotation interval and because the stimulus intensity is held constant for each rotation interval. Averaging these physiological responses across each 5-minute interval allows a comparison between both physiological responses and malaise scores in later analyses. Because trainees vary in the number of minutes of rotation they tolerate during testing, the number of data points following initiation of rotation varies for each trainee in the linear regression analyses.

In addition, to determine if the rate of change of an autonomic response is related to the amount of time the individual tolerates the motion sickness test, Pearson product-moment correlation coefficients are computed to determine the relationship between the average slope of each autonomic response and the average number of minutes of rotation tolerated during the motion sickness tests.

Research using mental and physical stimuli other than motion sickness testing has demonstrated that autonomic responses are not only reproducible across repeated testing, but are influenced by the stimulus (stimulus response specificity) and the individual's characteristics (individual response stereotypy).

Stimulus response specificity (SRS) refers to the tendency for a stimulus to evoke a consistent pattern of physiological responses from a group of individuals. Individual response stereotypy (IRS) refers to the tendency that an individual has to respond with the same physiological pattern across a variety of stressors. The findings demonstrate reproducibility of autonomic responses across repeated testing of a single motion sickness stimulus.

Once this baseline process is completed, the trainees are given a number of training sessions totaling approximately six hours, over a three week period, and three rotating chair sessions (similar to the baseline test). The rotating chair sessions are given approximately 1 week apart, since this interval tends to eliminate the chance that physiological changes from session to session would be due to adaptation. Previous research has shown that adaptation occurs when testing is repeated within 48 hours however, adaptation does not tend to occur over longer intervals.

During each of these training sessions, a progress individual stress profile is prepared and stored in the AFTE system 10. The stress profiles are compared and the progress reviewed by the trainer who determines if the physiological parameters will be emphasized during subsequent training sessions.

At the completion of the training sessions, the trainee is asked to experiment with real life stress situations using the AFTE apparatus 22. The AFTE apparatus 22 stores the physiological responses of the trainee, which data is then downloaded (possibly by remote communication) to the CPU 17.

The post-training session is basically a follow-up session to ascertain that the trainee is managing his/her physiological responses as trained. During this post-training session, the rotating chair test is administered as before, and a stress profile prepared.

The trainee is also trained to gradually minimize his/her dependence on the visual monitor and to transfer his/her learning and applying it to real life situations.

Another application for the present AFTE method and system is to assist in the prevention or counteraction of postflight orthostatic intolerance (low blood pressure). Postflight orthostatic intolerance has been identified as a serious biomedical problem associated with long-duration exposure to microgravity in space. High priority has been given to the development of countermeasures for this disorder that are both effective and practical. Clinical research has demonstrated that people can be taught to increase their own blood pressure voluntarily, and that this could be an effective treatment for chronic orthostatic intolerance in paralyzed people. The present AFTE method is designed to examine the feasibility of adding training in control of blood pressure to an existing preflight training program for facilitating astronaut adaptation to microgravity and readaptation to earth gravity.

In a preliminary study three men and two women participated in four to nine AFTE sessions, each 15 to 30 minutes long. At the end of the training, the average increase in systolic and diastolic pressure, as well as mean arterial pressures, that the trainees made ranged between 20 and 50 mm Hg under both supine and 45° head-up tilt conditions. These findings indicate that the AFTE method may be a useful alternative or supplement to existing approaches for preventing postflight orthostatic intolerance.

AFTE may be an alternative for combating persistent pilot air sickness in high-performance military planes, and AFTE training may transfer from the rotating chair on the ground to the variety of maneuvers in military flight well enough to return aircrew members, who would otherwise have been permanently grounded, to active flying duty.

A recent pilot experiment conducted by NASA, the U.S. Army, and the Coast Guard investigators, examined the efficacy of physiological self-regulation training as a means of improving pilot performance during emergency flying conditions. In this experiment, a training group contained pilots of HC-130 Hercules aircraft and HH-65 Dolphin helicopter. The control group contained about the same number of pilots. During an initial flight (search and rescue emergency flying scenario), physiological data were recorded on each crewmember and individual crew performance was rated by an instructor pilot. The crewmembers of the training group were then taught to regulate their own physiological response levels using the present AFTE method. The crewmembers of the control group received no AFTE training. During a second flight, the crewmembers of the training group showed significant improvement in performance, while those of the control group did not.

The operation of the AFTE system 10 will now be described in more detail in relation to the flow charts in FIGS. 14–17. It should be understood that the operation of the AFTE apparatus 22 is the same as, or similar to that of the AFTE system 10. The AFTE system 10 starts at 1100 by opening the personal management file where data and personal information previously stored on the CPU 17 or 23 are made available for use, processing and update. The AFTE system 10 is then initiated at 1101 to start collecting data on all the selected biological parameters. While only a few of these biological parameters will be described in conjunction with the operation of the AFTE system 10, it should be understood to one of ordinary skill in the art that other parameters can be selected as well. A feature of these biological parameters could be that they can either be measured or calculated.

The AFTE system 10 inquires at 1102 about the occurrence of a specific parameter. In this particular example the specific parameter is the cardiac R pulse or spike of the QRS complex. It should be clear that another specific parameter, a plurality of specific parameters, or a particular combination of specific parameters and parameter values may alternatively be used to initiate a timing cycle or to start the measurement or calculation of the desired parameters. The AFTE system 10 then continuously collects data throughout its operation.

When the R pulse is sensed or detected, an RR timer, or another preset timer is started at 1103. As used herein, RR interval or RR period refers to the time interval between two consecutive cardiac R pulses. As the AFTE system 10 continues to collect data, it inquires about the occurrence of the next R pulse at 1104. If the next R pulse does not occur within a predetermined or desired interval,may, but system 10 may, but not necessarily, ignore the data collected during this predetermined RR interval, and will restart the timer upon the occurrence of the next R pulse. On the other hand, when the next R pulse is sensed or detected, the AFTE system 10 almost simultaneously stops the RR timer, records the length of the RR interval, and resets the RR timer, as indicated at 1105, and further processes the collected data, as it will discussed hereafter.

For illustration purpose only, and without intent to limit the scope of the invention, the collected data is stored and processed at 1106 into the following desired parameters, which parameters and/or their average values may then be selectively displayed at 1107 to the trainer and/or the trainee. The parameters may be displayed on the monitors 19, 25 and/or the wrist display unit 30, as illustrated by an exemplary monitor screen 2000 shown in FIG. 17. The order in which the collected data is processed may vary from one application to another, and is not necessarily limited to the order described herein. The unprocessed or raw data may also be stored at 1108, in the CPU 17.

Figure 15:
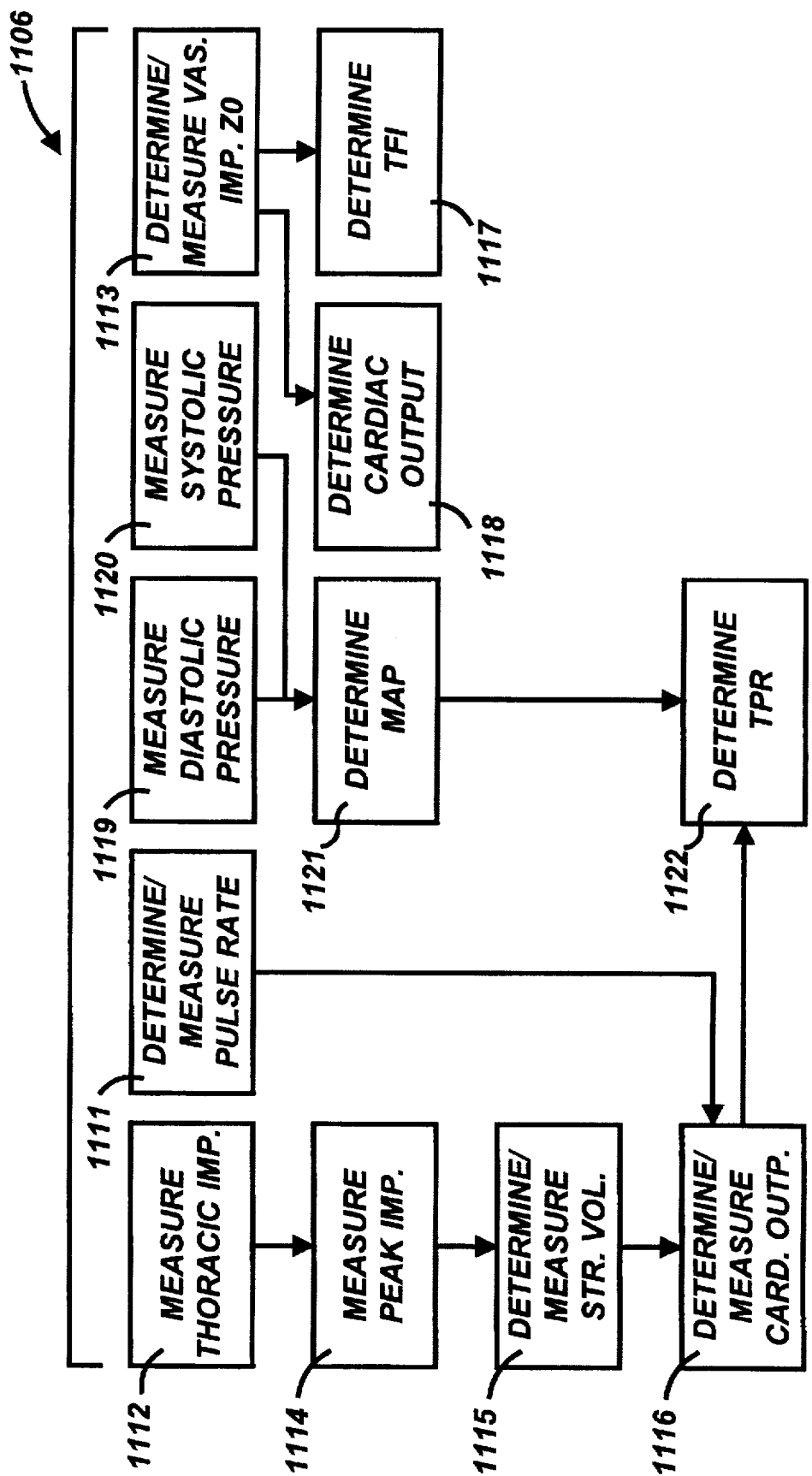
Figure 16:
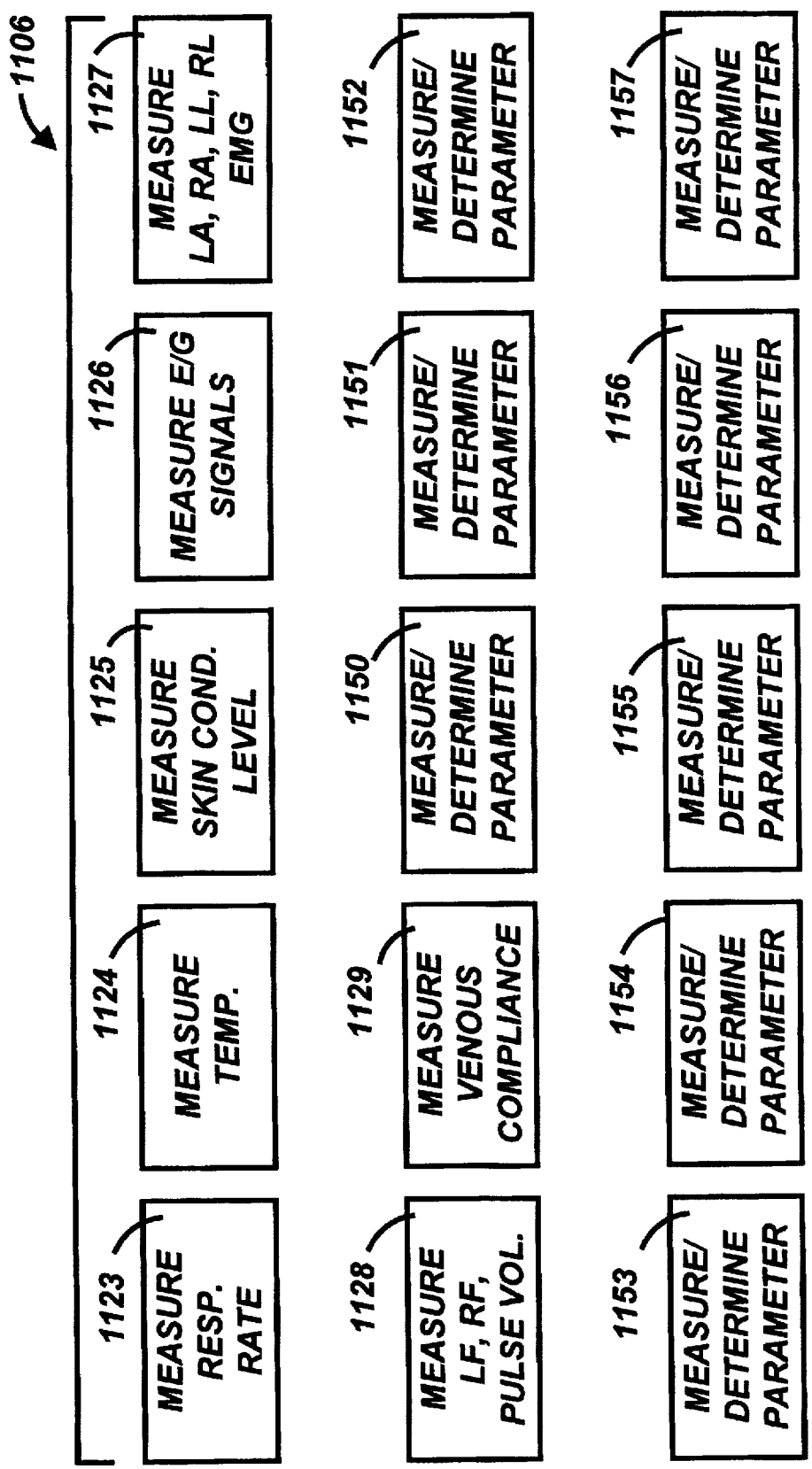

The processing step or routine 1106 of the collected data will now be described with reference to FIGS. 15 and 16. The AFTE system 10 determines the pulse rate of the trainee at 1111, according to the following equation:

$$\text{PulseRate} = \frac{1}{RR \text{ Interval}} \times 60.$$

The pulse rate is then stored and selectively displayed. In another embodiment, the pulse rate is averaged over a predetermined interval, for instance 30 seconds, and the average value may also be displayed.

The AFTE system 10 also measures the electrical impedance of the chest, i.e., the thoracic impedance $\Delta Z$ at 1112, and measures or determines the average or mean thoracic impedance, i.e., basal impedance Zo at 1113. The AFTE system 10 measures, at 1114, the peak or maximum value of the first derivative of the thoracic impedance $\Delta Z$ with respect to time:

$$\left( \frac{\partial Z}{\partial t} \right) \text{Max.}$$

It is well known that changes in the impedance of the thoracic cage correlate with changes in the blood stroke volume. The following equation generally approximates the relationship between the stroke volume and changes in the thoracic impedance:

$$\text{Stroke Volume} \propto \left( \frac{\partial Z}{\partial t} \right) \text{Max.}$$

As a result, the stroke volume and the cardiac output may be measured or determined, at 1115 and 1116, respectively, using various methods. One such method is to make a qualitative determination of the stroke volume, by directly correlating the stroke volume to the peak value of the first derivative of the thoracic impedance $\Delta Z$ with respect to time.

Another method for determining the cardiac output is for the AFTE system 10 to calculate the stroke volume of the trainee based on the following equation:

$$\text{STROKE VOLUME} = \frac{\left( \frac{\partial Z}{\partial t} \right) \text{Max.} \cdot \rho \cdot L^2 \cdot TVE}{Zo^2}$$

In the above equation, $\rho$ is the specific resistance of blood, which, for the purpose of this example, will be considered constant and equal to 150 Ohm-cm. $L^2$ is the square of the distance L between the voltage electrodes, through which a constant current, such as I=1 mA at 50 KHz passes. TVE refers to the time for ventricular ejection, which is also known as the ventricular ejection time (VET). TVE corresponds to the time interval between the onset of the closing of the heart AV valve until the closing of the aortic and pulmonary valves. In the present example, the TVE generally corresponds to the time interval between two consecutive heart sounds. It has been demonstrated that the TVE variability between individuals is generally within the range of two percent (2%), and therefore, for the purpose of this example, the TVE will be presumed to be constant. The basal impedance Zo is a generally measurable constant impedance.

In another embodiment, the stroke volume is averaged over a predetermined interval, for instance 30 seconds, and the average value may also be displayed.

The AFTE system 10 then calculates, or in another embodiment measures the cardiac output according to the following equation:

$$\text{CARDIAC OUTPUT} = \text{STROKE VOLUME} \times \text{PULSE RATE}$$

The thoracic fluid index (TFI) is determined at 1117 pursuant to the following equation:

$$TFI = \frac{1}{Zo^2}$$

The thoracic fluid index TFI is an indication of the amount of fluid present in the chest (thorax). The cardiac output is determined at 1118.

The AFTE system 10 selectively displays the stroke volume, the cardiac output and TFI. In another embodiment, the stroke volume, the cardiac output and TFI are averaged over a predetermined interval, for instance 30 seconds, and the average values may also be displayed.

The AFTE system 10 also measures the diastolic and the systolic pressures at 1119 and 1120, respectively, and then calculates the mean arterial pressure MAP therefrom, at 1121, according to the following equation:

$$MAP = \frac{\text{SYSTOLIC PRESSURE} - \text{DIASTOLIC PRESSURE}}{3} + \text{DIASTOLIC PRESSURE}$$

The AFTE system 10 selectively displays the diastolic pressure, the systolic pressure, and the MAP. In another embodiment, the diastolic pressure, the systolic pressure, and the MAP are averaged over a predetermined interval, for instance 30 seconds, and the average values may also be displayed.

Having determined the MAP and the cardiac output, the AFTE system 10 can approximate the value of the total peripheral pressure, which is an autonomic response, at 1122, according to the following equation:

$$TPR = \frac{MAP}{\text{CARDIAC OUTPUT}}$$

In this particular example, TPR is displayed in real time, and, in another embodiment, it may be averaged and the average value displayed.

The AFTE system 10 further measures the trainee's respiration rate at 1123 using one of several available methods. One such method includes the use of a strain gauge placed around the trainee's waste. Another method is to derive the respiration rated from the thoracic impedance and impedance changes described above. Other methods may also be used. The respiration rate may be displayed on a real time basis, or, in the alternative, it could be average and its average value displayed.

Similarly, the AFTE system 10 measures the trainee's temperature, skin conductance level, and electrogastrogram signals at 1124, 1125 and 1126, respectively. These measured values may be selectively displayed to the trainer and/or to the trainee or user, or, alternatively, they may be averaged, and their average values selectively displayed.

In addition, the AFTE system 10 measures the electromyogram (EMG) signals at one or more limbs at 1127. In this particular example, the AFTE system 10 measures the EMG signals from the left arm, right arm, left leg and right leg in order to measure the muscle activities in these limbs. The measured EMG signals are preferably processed, such as by rectification, filtering, and possibly averaging over a predetermined time interval, so as to produce a more detectable and measurable envelope. The processed EMG signals may then be selectively displayed.

Each cardiac beat triggers the AFTE system 10 to measure the pulse volumes at one or more parts of the trainee's body at 1128. The measured values provide qualitative or relative indications of the amount of blood flowing through a particular body part with each cardiac pulse. Several methods are available to measure the pulse volume. One such method includes the use of a photoplethysmograph connected to selected body parts, such as the left and right fingers (LF, RF). Another method includes the use of a laser, which operates similarly to the photoplethysmograph but is less susceptible to noise. Yet another method is the use of the Doppler effect to measure the pulse volume in another extremity, for instance the temporal region, to determine the volume of blood flowing to the head. The measured pulse volumes may be selectively displayed on real time basis; however, since they display a wide excursion range, it would be preferable to integrate and average them over a predetermined interval, such as the RR interval, and to selectively display their average values rather than their instantaneous values.

Another exemplary parameter that may be monitored and measured by the AFTE system 10 is the Venous compliance, which is indicative of the body part's capability to store fluid, according to the following equation:

$$\text{VENOUS COMPLIANCE} = \frac{\partial V}{\partial P}$$

where δV is the pulse volume measured by the AFTE system 10, as explained above, and δP is the change in blood pressure. The Venous compliance parameter or its average may be selectively displayed to the trainer and/or the trainee.

The empty boxes 1150 through 1157 show that the AFTE system 10 may measure and/or determine other parameters, such as those that have been described previously.

Figure 17:
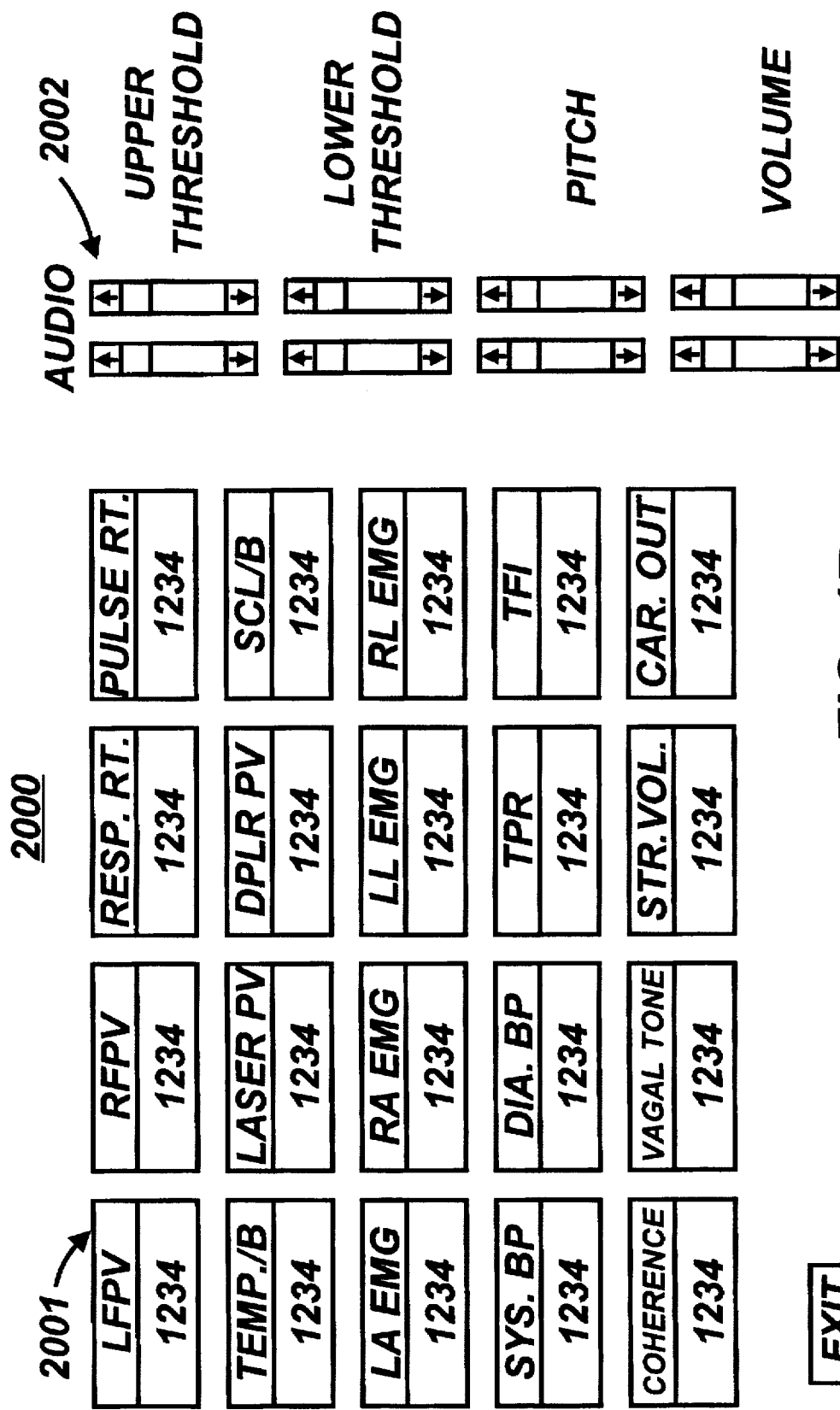

The step of graphically displaying the processed parameters 1107 (FIG. 14) will now be described in relation to FIG. 17. The exemplary monitor screen 2000 of FIG. 17 is shown herein for illustration purpose. It includes two main sections: a parameter section 2001 and an audio section 2002. The trainer selects the parameters to be displayed on the trainer's monitor 19 and the trainee's monitor 25, and optionally on the wrist display unit 30. As previously indicated, the displayed parameters may be the actual instantaneous parameters that are measured or determined, or their average values. The parameters displayed on the trainer's monitor 19 do not necessarily correspond to the parameters displayed on the trainee's monitor 25, since the trainer determines which parameters are displayed on the trainee's monitor 25. Ultimately, the trainee determines the parameters to be displayed on the wrist display unit 30, when he/she uses the AFTE apparatus 22 independently from the trainer.

The following is a list of the parameters displayed on the monitor screen 2000:
LFPV: Left Finger Pulse Volume.
RFPV: Right Finger Pulse Volume.
RESP. RT.: Respiration Rate.
PULSE RT.: Pulse Rate.
TEMP./B: Temperature.
LASER PV: Laser Pulse Volume.
DPLR PV: Doppler Pulse Volume.
SCL/B: Skin Conductance Level.
LA EMG: Left Arm EMG.
RA EMG: Right Arm EMG.
LL EMG: Left Leg EMG.
RLL EMG: Left Leg EMG.
SYS. BP: Systolic Blood Pressure.
DIA. BP: Diastolic Blood Pressure.
TPR: Total Peripheral Pressure.
TFI: Thoracic Fluid Index.
STR. VOL.: Stroke Volume.
CAR. OUT.: Cardiac Output.
Vagal Tone.
Coherence between respiration and heart rate.

Analysis of the weighted coherence parameter was performed in 1980 by Porges et al., between the heart rate and respiration. Estimates of the cardiac vagal tone resulted from an analysis performed in 1985 by Porges, from the amplitude of respiratory sinus arrhythmia as seen in heart rate data. Cross spectral analyses (BMDPIT) were used to generate a coherence function, a measure of covariation between heart rate and respiration. Then a weighted coherence was derived by weighting the coherence function across a band of frequencies (>0.1, <0.4 Hz) by the spectral densities. The weighted coherence may provide a quantitative estimate of stretch receptor influence on heart rate activity. Estimate of cardiac vagal tone were derived by spectral analysis of heart rate epochs. First, a third order moving polynomial window (10 seconds) was applied to the heart rate series to remove aperiodic trends, then the series was bandpass filtered (>0.1, <0.4 Hz) to allow nominal respiratory frequencies to pass, and finally the new heart rate series was subjected to spectral analysis to obtain estimates of the vagal tone.

The audio section 2002 includes various control levels that enable the trainer to regulate the voice and tone communication with the trainee. Normally, the audio section 2002 is not displayed on the trainee's monitor 25.

The following is a prototype firmware or software program, hereinafter referred to as AFTE firmware, used for processing and editing raw data collected during ambulatory sessions with the AFTE apparatus 22.

The AFTE firmware can be broken down into two portions: initialization and process. Initialization occurs only once during power up. All variables, registers and devices such as the LCD (liquid crystal display) driver of the wrist display unit 30, are initialized for proper operation. After this portion is complete the controller "goes to sleep" waiting for a real time interrupt. The controller "wakes up" and begins executing the infinite loop of runtime code. After passing through one complete loop, the controller moves into the "sleep" state, conserving energy waiting for the next interrupt.

The process portion of the code has three primary operating modes: subject, controlled, and configuration. Moving into the configuration mode can be done only during power up. Connecting a terminal to the AFTE apparatus 22 via a communication interface box with the switch placed in the ATTENTION position brings up the CONFIGURE menu on the terminal. Signal processing is not performed in this mode. The AFTE apparatus 22 is simply servicing the requests of a terminal.

The subject and controlled modes enable signal processing of the biological signals. The difference between the two modes is evident only on the LCD of the wrist display unit 30. In controlled mode, the LCD shows all zeros, suppressing all feedback to the user. In subject mode the signal processing results are displayed on the LCD. The AFTE apparatus 22 toggles between the two modes each time the AFTE apparatus 22 powers up with an EVENT button depressed. The EVENT button must remain depressed for five seconds during power up in order to change the mode. Switching modes is evident by observing the LCD.

The AFTE apparatus 22 also determines the LCD and the data recorder 67 functionality If communication between the LCD and the controller has halted. The routine sets an error bit and records the time of LCD malfunction to the data recorder 67. If the error bit is set, the code attempts to reinitialize the LCD during each real time interrupt. A successful reinitialization resets the error bit. A data recorder 67 malfunction is sensed if a pinch roller on the data recorder 67 fails to rotate. The failure of an edge detect within TACHOUT interrupts at the controller, causes a data recorder failure indicator to light on the LCD. A successful edge detect at the controller resets a malfunction indicator on the LCD.

A low battery sense is also handled by the AFTE apparatus 22. If voltages from the battery are below the threshold level, the respective indicator on the LCD is illuminated, and the system low battery code LBSYSCODE is sent to the data recorder 67.

Every second (REFRESH interrupts) the SCL (skin conductance level) is determined. The value in the pulse accumulator is passed on to the CALCMHO routine for translation to a standard unit skin conductance value. The value returned from CALCMHO is passed on to the LCD for display.

The accelerometer routine found in the AFTE apparatus 22 checks if acceleration in any of the three axes is within bounds. If the A/D (analogue to digital) value on any axis is not in the range of 20 to 230, the respective LCD indicator (X, Y, or Z) is illuminated.

The timecode prioritizer section of the code is closely linked with the TIMECODE subroutine. This portion of code first ensures that the data recorder 67 is not running calibration, and that no other functions are sending time code. If both cases are true then the word CODES is scanned for timecode requests. If a routine wishes to send data to the data recorder 67, it sets its associated bit in the CODES word. The prioritizer finds the highest priority bit set in CODES (bit 0 has the highest priority and bit 15 has the lowest), and loads the associated data into the TPCODE byte. The TIMECODE subroutine is then requested to relay this data to the data recorder 67. Completing data transmission is signified by clearing the associated bit in the CODES word. The routine is then ready to scan the word again looking for the next set bit. If all bits are reset the routine does nothing.

The routines that are utilized by the AFTE apparatus 22 are as follows: TIMECODE, CALCMHO, SETDISP, LCDINIT, SWITCH, RTCINTS, TEACCAL, EVENT, SEQUENCE, LOWBAT, and PROCED.

PROCED Routine: A proceed module contains the "Respiration Routine", "Heart Rate Routine", "Temperature Routine", and "BVP routine" (BVP stands for blood volume pulse). In the normal mode of operation, the Respiration algorithm is executed, followed by Heart rate and finally BVP. In the event button is held down for a period of time (refer to EVENT routine), the temperature algorithm is executed in place of the BVP algorithm. The BVP algorithm begins execution once again if the event button is held down for the same duration of time.

The respiration routine is responsible for determining the rate of respiration to the nearest integer and displaying this rate to the LCD of the wrist display unit 30. Due to the limited amount of RAM available in the digital system, a desirable method for determining the respiration rate in the AFTE apparatus 22 involves a linear regression of consecutive data points. Other DSP methods such us FFT's (Fast Fourier Transforms) are optional.

Each time the respiration routine is called, such as every 8.19 ms, the A/D value is read and added to a running sum. After n points are gathered, the average is calculated and presented to the linear regression routine. The linear regression routine (referred to as PROCESS in the software listing) looks at a window of the past × averages from which it determines the slope. The value of the slope of the A/D output as well as the sign of the slope (+, −, 0) is returned to the respiration routine. The sign of the slope is zero if the magnitude of the slope is less than the parameter RSLPTHR. If the magnitude is greater than or less than RSLPTHR the linear regression routine returns positive or negative respectively.

The backbone of the respiration routine is to detect alternating positive and negative slopes via the linear regression method. Each time a negative slope is detected, the time is recorded and the routine begins looking for a positive slope. The period between two consecutive negative slopes is translated into the breathing rate with units of breaths per minute. The variable RSPPTS determines the number of consecutive rates averaged together to form the rate presented to the display. If the routine fails to detect the next slope under scrutiny before RTIMOUT seconds occur the routine sends the display a no-signal indicator.

The negative slopes are chosen to mark the beginning of a new breath cycle because of the more definitive exhalation portion of the wave. Slow inhalation often has an unsmooth characteristic, giving way to an uncertainty in the positive slope detect location. The detection variance between two positive slopes on a constant breathing rate gives way to a larger error than its negative slope counterpart.

The parameters of the routine are optimized to detect rates in the range of 6 to 35 bpm (the analog filter characteristics are in agreement with this range). Ten sample points are averaged into one data point and result in optimal noise rejection characteristics while preserving the wave shape. Linear regression performed on seven of these data points, which, in this particular design represent the maximum value allowed before overflow occurs, optimize the routine for rate detection, giving the program the ability to tag consistent positive and negative slopes on constant rate waves. Three consecutive breathing rates are averaged together and form the current respiration which is presented to the LCD for display, concluding one cycle of the algorithm.

The blood volume pulse (BVP) routine is responsible for determining the relative amplitude of each pulse and displaying the result on the LCD display. The basic routine can be found in the PROCESS module of the code following the Heart Rate code.

The BVP algorithm has much in common with the respiration algorithm. The routine uses linear regression to determine alternating positive and negative slopes. By setting the threshold values large enough (determined experimentally), the routine is able to detect the positive and negative edges of the pseudo R-wave portion of the BVP signal. The BVP signal at the A/D channel, however, is an inverted function of the signal produced by the finger transducer. Therefore, a negative slope detect corresponds to a positive slope detect on the true BVP signal.

The routine averages BVSAMP sample points into one data point, storing this value into the BV buffer. The buffer contains a moving window of the last BVSLPS data points. Each time a new data point is entered to the top of the buffer the routine calls the PROCESS routine to calculate the relative slope of the data points. Each time a positive slope is detected the routine marks the event, enables the heart on the LCD, and sets a flag to begin searching for a negative slope.

The backbone of the routine is relative volume detection, a number In the range of 0 to 256. The routine keeps track of the maximum and minimum values found during one complete pulse cycle. A new pulse cycle begins on the detection of a positive slope, at which time the difference between the maxima and the minima is determined. This difference is averaged together with the past BVPTS differences and presented to the display. A positive slope detect also lights the heart on the display to signify a heart beat. After ¼ second the routine turns the heart signal off again.

The heart rate of the routine is responsible for determining the rate of the incoming signal and displaying the result on the LCD. The heart rate algorithm relies, once again, on the linear regression routine to determine the slope of the incoming signal. The time between two positive slopes is translated into the heart rate. Unlike the BVP and respiration routine, the heart rate algorithm looks for a positive, zero, and negative slope transition. The routine must pass through all three slope detects, before the signal is considered valid.

HRSAMP points are averaged together to form one data point. A moving window of the latest HRSLPS data points are processed with the linear regression routine. If the magnitude of the slope is larger than HRSLPTHR then the slope is considered positive or negative. If the slope magnitude is less than HRSLPTHR, the slope is zero. The routine averages the latest HRPTS heart rates, and displays this value on the LCD.

The temperature routine is responsible for determining the temperature and displaying the result to the LCD. The routine sums up TSUMUP temperature sample points, and then performs the function:

Temperature=GAIN*SUM+OFFSET in floating point arithmetic. The values of GAIN and OFFSET are determined by the "tempcal" routine. The temperature value is sent to the display each time the value is calculated.

The routine has the capability to run in two different modes, if the AFTE apparatus 22 is connected to a terminal and receives a carriage return character, the routine takes integral average of the last TSUMUP samples, in other terms, the routine displays the average A/D value to the display. This portion of the algorithm is added to aid in the calibration of the AFTE apparatus 22, which toggles between the two modes of display each time a carriage return character is detected.

Linear Regression is the mathematical method for determining the best fit straight line for a set of data points. Since the signals received from the biological transducers are often noisy, and the purpose is mainly to find the trend of the incoming signals, the least square method becomes particularly appealing. The program utilizes the following linear regression equations:

$$\sum_{i=0}^{n} Yi = na + b \sum_{i=0}^{n} Xi$$

$$\sum_{i=0}^{n} XiYi = a \sum_{i=0}^{n} Xi + a \sum_{i=0}^{n} Xi^2.$$

Solving for the slope, one obtains the following equation:

$$b = \frac{\sum_{i=0}^{n} Xi * \sum_{i=0}^{n} Yi - n \sum_{i=0}^{n} Xi * Yi}{\left(\sum_{i=0}^{n} Xi\right)^2 - n \sum_{i=0}^{n} Xi^2}$$

Realizing that the bottom of the equation is a constant (sampling is performed on every interrupt) and serves as nothing more than a negating scaling factor the equation becomes:

$$b = n \sum_{i=0}^{n} Xi * Yi - \sum_{i=0}^{n} Xi * \sum_{i=0}^{n} Yi.$$

The above equation is directly implemented in assembly code within the PROCESS routine. In the present design, the code does not prevent overflow which will result if n is set to a value larger than 7. Also, removing the scaling factor from the above equation causes the slope value calculated by the PROCESS routine to be dependent on the value n. Increasing the value of n will increase the value of the slope. Therefore, the slope thresholds should be increased with an increase in the value of n.

Other routines which call the PROCESS routine, must first setup the appropriate memory spaces and pointers. The Y-register must point to the buffer which contains the data information, the location LENGTH must be initialized with the number of points to be analyzed, and SLPTHR is set with the desired slope thresholds. After calling PROCESS the routine, the buffer which is passed contains the updated slope value and slope value (negative, positive or zero).

TIMECODE is responsible for sending data and time to the temperature channel on the data recorder 67. Data is sent to the data recorder 67 in a serial digital format where the bit width is as follows:

bit width=(7*8.19 ms)=57.33 ms.

This slow rate of transmission is chosen on the basis on the data recorder limited recording bandwidth.

Timecode is sent in two formats. The first is the minute timecode. Each time a minute passes, a ⅓ second pulse is delivered to the data recorder 67. The second format is the complete timecode information. This data is sent hourly or as a result of a significant event, such as low battery, LCD malfunction, or EVENT button depression. The time and data format is sent as follows:

| 1) Start Mark | 20 bits | (HIGH) |
|---|---|---|
| 2) Time Mark | 1 bit | (LOW) |
| 3) Ones of seconds | 4 bits | (BCD) |
| 4) Tens of seconds | 4 bits | (BCD) |
| 5) Ones of minutes | 4 bits | (BCD) |
| 6) Tens of minutes | 4 bits | (BCD) |
| 7) Ones of hours | 4 bits | (BCD) |

-continued

| 8) Tens of hours | 4 bits | (BCD) |
| 9) One of days | 4 bits | (BCD) |

While specific embodiments of the autogenic-feedback training exercise (AFTE) method and system have been illustrated and described in accordance with the present invention, modifications and changes of the apparatus, parameters, and composition, use and operation will become apparent to those skilled in the art, without departing from the scope of the invention.

What is claimed is:

1. An autogenic-feedback training exercise (AFTE) multi-parameter physiological conditioning system for training a trainee to gain better control of a plurality of the trainee's physiological responses by using two combined self-regulatory techniques, biofeedback and autogenic therapy, and to permit the trainee to voluntarily and simultaneously control the physiological responses, the system comprising in combination:

a trainer sub-system for use by a trainer and including a processor;

a trainee sub-system for use by the trainee, including an AFTE apparatus connected to said trainer sub-system;

said AFTE apparatus including a sensor assembly for sensing baseline values of a plurality of physiological parameters indicative of the trainee's physiological responses, and for further sensing changes in said physiological parameters when the trainee is under stress and during training, in order for said trainer sub-system to develop an individual stress profile for the training;

said AFTE apparatus further comprising an ambulatory, physiological-monitoring apparatus; and based on said stress profile, said trainer sub-system selectively feeding back one or more of said plurality of physiological parameters to said trainee sub-system, in order to enable the trainee to simultaneously modify and control hierarchy, magnitude and phase relationships of the physiological responses corresponding to said plurality of fed back physiological parameters, so as to normalize the physiological responses by minimizing variances of the physiological responses from their corresponding baseline values.

2. The system according to claim 1, wherein said trainer sub-system selects a physiological parameter and delineates its tonic and phasic properties.

3. The system according to claim 1, wherein said AFTE apparatus further includes a display unit capable of selectively displaying analog and digital numerical displays of the trainee's physiological parameters.

4. The system according to claim 3, wherein said trainer sub-system further includes a monitor for selectively displaying at least some of said trainee's physiological parameters.

5. The system according to claim 1, wherein audio and data communication between the trainer sub-system and the trainee sub-system is maintained via a data bus.

6. The system according to claim 5, wherein said data bus includes a remote communication link.

7. The system according to claim 6, wherein said AFTE apparatus further includes a belt assembly comprised of system electronic circuitry; and wherein said belt assembly includes a modular package that houses the system electronic circuitry, and which is comprised of one or more interconnectable modules.

8. The system according to claim 7, wherein some of the physiological parameters to be displayed by said display unit, either simultaneously or separately are: blood volume pulse (BVP), skin temperature, heart rate, skin conductance level, and respiration rate.

9. The system according to claim 7, wherein said modules include:

a first module that contains electronic circuits for providing signal conditioning for electrocardiogram, skin conductance level, temperature, blood volume pulse, and respiration signals;

a second module which contains circuitry for a digital sub-system that:
processes physiological signals in real-time;
times AFTE sessions;
generates time and event codes;
multiplexes time and event codes with temperature data;
transmits a periodic time marker to a trainee sub-system processor;
interfaces with diagnostic equipment and said trainer sub-system processor;
configures system operating modes; and
amplifies signals from said sensor assembly;

a third module that collects system inputs from said sensor assembly, and that relays said inputs to said first and second modules; and a fourth module that includes a power source that supplies power to said AFTE apparatus.

10. The system according to claim 6, wherein said sensor assembly includes at least one ECG electrode for monitoring the trainee's cardiac electrical impulses.

11. The system according to claim 10, wherein said sensor assembly further includes at least one skin conductance level (SCL) electrode for monitoring changes in the electrical conductivity properties of the trainee's skin.

12. The system according to claim 10, wherein said sensor assembly further includes a respiration transducer for detecting changes in the trainee's thoracic cavity size caused by the expansion and contraction of the diaphragm, and for monitoring the frequency of respiration.

13. The system according to claim 10, wherein said sensor assembly further includes a triaxial accelerometer for measuring gross head movements in three directions.

14. The system according to claim 10, wherein said sensor assembly further includes a transducer for measuring skin temperature and a sensor for detecting blood volume pulse.

15. The system according to claim 10, wherein said sensor assembly further includes blood pressure measuring apparatus for measuring the trainee's systolic and diastolic blood pressures.

16. The system according to claim 10, wherein said sensor assembly further includes at least one of the following sensors:

impedance cardiograph for providing a reliable index of (a) stroke volume, (b) contractility, (c) cardiac output, and (d) systolic timing intervals;

impedance plethysmograph for monitoring the trainee's lower limb volume;

electromyograph (EMG) for monitoring the muscle activity of the trainee's legs;

electromyograph for monitoring the muscle activity of the trainee's arms;

electroencephalography (EEG) for monitoring the trainee's brain electrical potentials;

electro-oculography (EOG) for monitoring the trainee's eye movements;

electrogastrography (EGG) for monitoring the trainee's gastrointestinal smooth muscle surface potentials.

17. An autogenic-feedback training exercise (AFTE) multi-parameter physiological conditioning method for training a trainee, to gain better control of a plurality of the trainee's physiological responses by using two combined self-regulatory techniques, biofeedback and autogenic therapy, and to permit the trainee to voluntarily and simultaneously control the plurality of physiological responses, the method comprising:

using a trainee sub-system formed of an AFTE apparatus connected to a trainer sub-system and including a sensor assembly for sensing baseline values of a plurality of physiological parameters indicative of the trainee's physiological responses and for further sensing changes in said physiological parameters when the trainee is under stress and during training, in order for said trainer sub-system to develop an individual stress profile for the trainee;

based on said stress profile selectively feeding back one or more of said plurality of trainee's physiological parameters to said trainee sub-system, in order to enable the trainee to simultaneously modify and control hierarchy, magnitude and phase relationships of the physiological responses, so as to normalize the plurality of physiological responses by minimizing variances of the physiological responses from their corresponding baseline values;

said step of using said trainer sub-system providing a sequence of baseline, training and post-training sessions;

said step of providing a baseline session includes selecting at least one of the following steps, and using the selected steps in a predetermined order:

reducing extrinsic stimuli;

determining the trainee's optimal range of physiological parameters at rest to obtain that trainee's individual baseline profile;

gradually increasing and decreasing stimulus levels to determine the trainee's range of physiological parameters under stress, and the relationship of these parameters;

determining the order of change of the physiological parameters change under stress;

determining the magnitude of response and the tonic and phasic relationship of the physiological parameters under stress;

determining the developing symptoms and correlating them to accompanying changes in the physiological parameters;

obtaining the trainee's individual profile or specific response pattern under stress;

training the trainee to use passive concentration;

training the trainee to feel and pay attention to various bodily sensations;

training the trainee to focus using passive attention;

providing a baseline test, starting with a specific autogenic exercise;

training the trainee to normalize his/her individual profile and to modify his/her behavior; and wherein said step of determining the trainee's optimal range of physiological parameters at rest includes having the trainer select at least one of the following six autogenic exercises:

1. Heaviness in the arms and legs;
2. Warmth in the periphery;
3. Regulated respiration;
4. Regulated heart beat;
5. Warmth in the solar plexus;
6. Coolness in the forehead.

18. The method according to claim 17, wherein said step of determining the developing symptoms includes the steps of:

having the trainee report his/her symptoms at predetermined intervals; and grading said symptoms.

19. The method according to claim 18, wherein said step of gradually increasing and decreasing the stimulus levels causes a corresponding increase or decrease of the trainee's physiological response levels, which enables the trainer to make at least some of the following determinations:

the trainee's range of physiological parameters under stress;

the relationship of these parameters;

the order of change of the physiological parameters;

the magnitude of response and the tonic and phasic relationship of the physiological parameters;

the developing symptoms; and to correlate these symptoms to accompanying changes in the physiological parameters; and wherein said step of correlating the symptoms and the physiological parameters includes the step of grading the trainee's symptoms based on self-report and the trainer's observation of several subjective symptoms such as body temperature, dizziness, headache, drowsiness, sweating, pallor, salivation, and nausea.

20. The method according to claim 19, wherein said step of providing a training session includes the steps of:

training the trainee to normalize his/her physiological responses by simultaneously modifying and controlling the hierarchy, magnitude and phase relationship these several physiological responses, aiming at keeping the levels of these physiological responses at, or close to that trainee's individual baseline profile, under stress, in order to alleviate or prevent the developing symptoms; and training the trainee to maintain normal regulation of the autonomic nervous system by maintaining balance between the two branches of the autonomic nervous system: the sympathetic and the parasympathetic branches.

21. An autogenic-feedback training exercise (AFTE) multi-parameter physiological conditioning method for training a trainee to gain better control of a plurality of the trainee's physiological responses by using two combined self-regulatory techniques, biofeedback and autogenic therapy, and to permit the trainee to voluntarily and simultaneously control the plurality of physiological responses, the method comprising:

using a trainee sub-system formed of an AFTE apparatus connected to a trainer sub-system and including a sensor assembly for sensing baseline values of a plurality of physiological parameters indicative of the trainee's physiological responses and for further sensing changes in said physiological parameters when the trainee is under stress, and during training, in order for said trainer sub-system to develop an individual stress profile for the trainee;

based on said stress profile selectively feeding back one or more of said plurality of trainee's physiological parameters to said trainee subsystem, in order to enable the trainee to simultaneously modify and control hierarchy, magnitude and phase relationships of the physiological responses, so as to normalize the plurality of physiological responses by minimizing variances of the physiological responses from their corresponding baseline values;

said step of using said trainer sub-system providing a sequence of baseline, training and post-training sessions;

said step of providing baseline session includes selecting at least one of the following steps, and using the selected steps in a predetermined order:

reducing extrinsic stimuli;

determining the trainee's optimal range of physiological parameters at rest to obtain that trainee's individual baseline profile;

gradually increasing and decreasing stimulus levels to determine the trainee's range of physiological parameters under stress, and the relationship of these parameters;

determining the order of change of the physiological parameters change under stress;

determining the magnitude of response and the tonic and phasic relationship of the physiological parameters under stress;

determining the developing symptoms and correlating them to accompanying changes in the physiological parameters:

obtaining the trainee's individual profile or specific response pattern under stress;

training the trainee to use passive concentration;

training the trainee to feel and pay attention to various bodily sensations;

training the trainee to focus using passive attention;

providing a baseline test, starting with a specific autogenic exercise;

training the trainee to normalize his/her individual profits and to modify his/her behavior; and wherein said step of training the trainee to normalize his/her physiological includes the steps of:

identifying one or more leading physiological responses under stress, and one or more trailing physiological responses under stress; and placing emphasis on training the trainee how to normalize said one or more leading physiological response simultaneously with said one or more trailing physiological responses.

22. An autogenic-feedback training exercise (AFTE) multi-parameter physiological conditioning method for training a trainee to gain better control of a plurality of the trainee's physiological responses by using two combined self-regulatory techniques, biofeedback and autogenic therapy, and to permit the trainee to voluntarily and simultaneously control the plurality of physiological responses, the method comprising:

using a trainee sub-system formed of an AFTE apparatus connected to a trainer sub-system and including a sensor assembly for sensing baseline values of a plurality of physiological parameters indicative of the trainee's physiological responses and for further sensing changes in said physiological parameters when the trainee is under stress and during training, in order for said trainer sub-system to develop an individual stress profile for the trainee;

based on said stress profile selectively feeding back one or more of said plurality of trainee's physiological parameters to said trainee sub-system, in order to enable the trainee to simultaneously modify and control hierarchy, magnitude and phase relationships of the physiological responses, so as to normalize the plurality of physiological responses by minimizing variances of the physiological responses from their corresponding baseline values;

said step of using said trainer sub-system providing a sequence of baseline, training and post-training sessions;

said step of providing a baseline session includes selecting at least one of the following steps, and using the selected steps in a predetermined order:

reducing extrinsic stimuli;

determining the trainee's optimal range of physiological parameters at rest to obtain that trainee's individual baseline profile;

gradually increasing and decreasing stimulus levels to determine the trainee's range of physiological parameters under stress, and the relationship of these parameters;

determining the order of change of the physiological parameters change under stress;

determining the magnitude of response and the tonic and phasic relationship of the physiological parameters under stress;

determining the developing symptoms and correlating them to accompanying changes in the physiological parameters;

obtaining the trainee's individual profile or specific response pattern under stress;

training the trainee to use passive concentration;

training the trainee to feel and pay attention to various bodily sensations;

training the trainee to focus using passive attention;

providing a baseline test, starting with a specific autogenic exercise;

training the trainee to normalize his/her individual profile and to modify his/her behavior; and wherein said step of providing a training session further includes the step of preparing and comparing a plurality of stress profiles for the trainer to identify which of the physiological parameters will be emphasized during subsequent training sessions.

23. An autogenic-feedback training exercise (AFTE) multi-parameter physiological conditioning method for training a trainee to gain better control of a plurality of the trainee's physiological responses by using two combined self-regulatory techniques, biofeedback and autogenic therapy, and to permit the trainee to voluntarily and simultaneously control the plurality of physiological responses, the method comprising:

using a trainee sub-system formed of an AFTE apparatus connected to a trainer sub-system and including a senior assembly for sensing baseline values of a plurality of physiological parameters indicative of the trainee's physiological responses and for further sensing changes in said physiological parameters when the trainee is under stress and, during training, in order for said trainer sub-system to develop an individual stress profile for the trainee; and, based on said stress profile selectively feeding back one or more of said plurality of trainee's physiological parameters to said trainee sub-system, in order to enable the trainee to simultaneously modify and control hierarchy, magnitude and phase relationships of the physiological responses so as to normalize the plurality of physiological responses by minimizing variances of the physiological responses from their corresponding baseline values; and wherein said step of using said trainee sub-system includes the steps of:
  starting to collect data on a selected one of said physiological parameters;
  starting a timer when said cardiac R pulse is sensed;
  inquiring about the occurrence of a subsequent R pulse;
  when said subsequent R pulse is sensed, almost simultaneously stopping said timer, recording the length of an RR interval, and resetting said timer; and
  processing said data that has been collected on a selected one of said physiological parameters.

24. The method according to claim 23, further including the step of displaying data representative of selected ones of said physiological parameters or the average values of said physiological parameters.

25. The method according to claim 24, wherein said steps of sensing baseline values of said plurality of physiological parameters, and changes in said physiological parameters includes the step of:
  determining the pulse rate of the trainee, according to the following equation:

$$\text{Pulse Rate} = \frac{1}{RR \text{ Interval}} \times 60.$$

26. The method according to claim 25, wherein said steps of sensing further include the steps of:
  measuring a thoracic impedance $\Delta Z$;
  measuring or determining the average or mean thoracic impedance, i.e., basal impedance $Z_o$; and
  measuring the peak or maximum value of the first derivative of the thoracic impedance $\Delta Z$ with respect to time:

$$\left(\frac{\partial Z}{\partial t}\right) \text{Max.}$$

27. The method according to claim 26, wherein said steps of sensing further include the step of determining the stroke volume by correlating the stroke volume and changes in the thoracic impedance, according to the following relationship:

$$\text{Stroke Volume} \propto \left(\frac{\partial Z}{\partial t}\right) \text{Max.}$$

28. The method according to claim 27, wherein said steps of sensing further include the steps of:
  determining the cardiac output, either by directly correlating the stroke volume to the peak value of the first derivative of the thoracic impedance $\Delta Z$ with respect to time, or by calculating the stroke volume based on the following equation:

$$\text{STROKE VOLUME} = \frac{\left(\frac{\partial Z}{\partial t}\right) \text{Max} \cdot \rho \cdot L^2 \cdot TVE}{Z_o^2}$$

where $\rho$ is the specific resistance of blood, $L^2$ is the square of the distance L between two voltage electrodes; TVE refers to the ventricular ejection time, and the basal impedance $Z_o$ is a generally measurable constant impedance;
  determining the cardiac output according to the following equation:

$$\text{CARDIAC OUTPUT} = \text{STROKE VOLUME} \times \text{PULSE RATE};$$

determining the thoracic fluid index (TFI) pursuant to the following equation:

$$TFI = \frac{1}{Z_o^2}.$$

29. The method according to claim 28, wherein said steps of sensing further include the steps of:
  measuring the diastolic and the systolic pressures;
  calculating a mean arterial pressure MAP according to the following equation:

$$MAP = \frac{\text{SYSTOLIC PRESSURE} - \text{DIASTOLIC PRESSURE}}{3} + \text{DIASTOLIC PRESSURE};$$

and
  determining a total peripheral pressure TPR, according to the following equation:

$$TPR = \frac{MAP}{\text{CARDIAC OUTPUT}}.$$

30. The method according to claim 27, wherein said steps of sensing further include the steps of:
  measuring the trainee's respiration rate, temperature, skin conductance level, electrogastrogram signals, electromyogram (EMG) signals at one or more limbs, pulse volume at one or more parts of the trainee's body, and the venous compliance according to the following equation:

$$\text{VENOUS COMPLIANCE} = \delta V/\delta P$$

where $\delta V$ is the pulse volume, $\delta P$ is the change in blood pressure.

31. An autogenic-feedback training exercise (AFTE) multi-parameter physiological conditioning method for training a trainee to gain better control of a plurality of the trainee's physiological responses by using two combined self-regulatory techniques, biofeedback and autogenic therapy, and to permit the trainee to voluntarily and simultaneously control the plurality of physiological responses, the method comprising:
  using a trainee sub-system formed of an AFTE apparatus connected to a trainer sub-system and including a sensor assembly for sensing baseline values of a plurality of physiological parameters indicative of the trainee's physiological responses and for further sensing changes in said physiological parameters when the trainee is under stress and during training, in order for said trainer sub-system to develop an individual stress profile for the trainee;
  based on said stress profile selectively feeding back one or more of said plurality of trainee's physiological parameters to said trainee sub-system, to in order to enable the trainee to simultaneously modify and control hierarchy, magnitude and phase relationships of the physiological responses, so as to normalize the plurality of physiological responses by minimizing variances of the physiological responses from their corresponding baseline values;
  said step of using said trainer sub-system providing a sequence of baseline, training and post-training sessions;
  said step of providing a baseline session includes selecting at least one of the following steps, and using the selected steps in a predetermined order:

reducing extrinsic stimuli;

determining the trainee's optimal range of physiological parameters at rest to obtain that trainee's individual baseline profile;

gradually increasing and decreasing stimulus levels to determine the trainee's range of physiological parameters under stress, and the relationship of these parameters;

determining the order of change of the physiological parameters change under stress;

determining the magnitude of response and the tonic and phasic relationship of the physiological parameters under stress;

determining the developing symptoms and correlating them to accompanying changes in the physiological parameters;

obtaining the trainee's individual profile or specific response pattern under stress;

training the trainee to use passive concentration;

training the trainee to feel and pay attention to various bodily sensations;

training the trainee to focus using passive attention;

providing a baseline test, starting with a specific autogenic exercise;

training the trainee to normalize his/her individual profile and to modify his/her behavior; and wherein said step of training the trainee to normalize his/her individual profile includes the step of selectively displaying at least one of the following parameters:

LFPV: Left Finger Pulse Volume;
RFPV: Right Finger Pulse Volume;
RESP. RT.: Respiration Rate;
HEART RT.: Heart Rate;
TEMP./B: Temperature;
LASER PV: Laser Pulse Volume;
DPLR PV: Doppler Pulse Volume;
SCL/B: Skin Conductance Level;
LA EMG: Left Arm EMG;
RA EMG: Right Arm EMG;
LL EMG: Left Leg EMG;
RLL EMG: Left Leg EMG;
SYS. BP: Systolic Blood Pressure;
DIA. BP: Diastolic Blood Pressure;
TPR: Total Peripheral Pressure;
TFI Thoracic Fluid Index;
STR. VoL.: Stroke Volume; and
CAR. OUT.: Cardiac output.

* * * * *